US008512948B2

(12) United States Patent (10) Patent No.: US 8,512,948 B2
Albitar et al. (45) Date of Patent: *Aug. 20, 2013

(54) COMPOSITIONS AND METHODS FOR DETECTING MUTATIONS IN JAK2 NUCLEIC ACID

(75) Inventors: Maher Albitar, Coto De Caza, CA (US); Wanlong Ma, Aliso Viejo, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 31 days.

This patent is subject to a terminal disclaimer.

(21) Appl. No.: 12/879,833

(22) Filed: Sep. 10, 2010
(Under 37 CFR 1.47)

(65) Prior Publication Data

US 2012/0003653 A1    Jan. 5, 2012

Related U.S. Application Data

(63) Continuation-in-part of application No. 12/503,318, filed on Jul. 15, 2009, and a continuation-in-part of application No. PCT/US2009/061691, filed on Oct. 22, 2009, which is a continuation of application No. 12/503,318.

(60) Provisional application No. 61/110,501, filed on Oct. 31, 2008.

(51) Int. Cl.
*C07H 21/04* (2006.01)
*C12Q 1/68* (2006.01)

(52) U.S. Cl.
USPC ......... 435/6.1; 435/6.11; 435/6.12; 435/91.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 5,639,611 A | 6/1997 | Wallace et al. | |
| 6,919,634 B2 | 7/2005 | Kuramoto et al. | |
| 2003/0092019 A1* | 5/2003 | Meyer et al. ...................... | 435/6 |
| 2007/0082332 A1 | 4/2007 | Mendrick et al. | |
| 2007/0149506 A1 | 6/2007 | Arvantis et al. | |
| 2007/0224598 A1 | 9/2007 | Chang | |
| 2007/0248961 A1 | 10/2007 | Albitar et al. | |

FOREIGN PATENT DOCUMENTS

WO    WO-2006/000482    1/2006

OTHER PUBLICATIONS

Sulong et al. (B. J. of Haematology, vol. 130, pp. 964-972, 2005).*
Yip et al. (Leukemia, vol. 20, p. 1165, 2006).*
Scott et al. (NEJM, vol. 356, No. 5, pp. 459-468, 2007).*
Inami et al. (Leukemia, vol. 22, pp. 216, 2008).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Nastiuk et al (Prostates, vol. 40, No. 3, pp. 172-177, 1999).*
Butcher et al. Leukemia, vol. 22, pp. 870-873, Oct. 2007.*
US Office Action dated Oct. 27, 2011 for U.S. Appl. No. 12/503,318.
Inami et al, Analysis of the exon 12 and 14 mutations of the JAK2 gene in Philadelphia chromosome-positive leukemia, Leukemia, 22:216, (2008).
US Office Action dated Jun. 3, 2011 in U.S. Appl. No. 12/503,318.
Abravaya, K., et al., Detection of point mutations with a modified ligase chain reaction (Gap-LCR), Nucleic Acids Research 23:675-682, (1995).
Baxter et al., Acquired mutation of the tyrosine kinase JAK2 in human myeloproliferative disorders, Lancet 365:1054-1061 (2005).
Boom, R., et al., Rapid Purification of Hepatitis B Virus DNA from Serum, J. Clin. Micro. 29:1804-1811, (1991).
Boom, R., et al., Rapid and Simple Method for Purification of Nucleic Acids, J. Clin. Micro. 28:495-503, (1990).
Buchman, G. W., et al., Selective RNA Amplification: A Novel Method Using dUMP-containing Primers and Uracil DNA Glycosylase, PCR Methods Applic. 3:28-31, (1993).
Cheung, R. C., et al., Rapid and Sensitive Method for Detection of Hepatitis C Virus RNA by Using Silica Particles, J. Clin Micro. 32:2593-2597, (1994).
Chirgwin, J. M., et al., Isolation of Biologically Active Ribonucleic Acid from Sources Enriched in Ribonuclease, Biochemistry, 18:5294-5299, (1979).
Chomczynski, P. and Mackey, K., Modification of the TRI Reagent !22 Procedure for Isolation of RNA from Polysaccharide-and Proteoglycan-Rich Sources, BioTechniques 19:942-945, (1995).
Chomczynski, P. and Mackey, K., Substitution of Chloroform by Bromochloropropane in the Single-Step Method of RNA Isolation, Analytical Biochemistry 225:163-164, (1995).
Chomczynski, P. and Sacchi, N., Single-Step Method of RNA Isolation by Acid Guanidinium Thiocyanate-Phenol-Chloroform Extraction, Analytical Biochemistry, 162:156-159, (1987).
Chomczynski, P., A Reagent for the Single-Step Simultaneous Isolation of RNA, DNA and Proteins From Cell and Tissue Samples, Biotech 15:532-537, (1993).
Cross, N.C., Competitive Polymerase Chain Reaction to Estimate the Number of BCR-ABL Transcripts in Chronic Myeloid Leukemia Patients After Bone Marrow Transplantation, Blood 82: 1929-36, (1993).
Fournié, G. J., et al., Recovery of Nanogram Quantities of DNA from Plasma and Quantitative Measurement Using Labeling by Nick Translation, Analytical Biochemistry, 158:250-256, (1986).
Giordanetto and Kroemer, Prediction of the structure of human Janus kinase 2 (JAK2) comprising JAK homology domains 1 through 7, Protein Engineering, 15(9):727-737 (2002).
Hage, "Immunoassays", Anal Chem., 71(12):294R-304R (1999).
Harpur et al., JAK2, a third member of the JAk family of protein tyrosine kinases, Oncogene, 7(7): 1347-1353, 1992.
Heid, et al., Real time quantitative PCR, Genome Res, 6: 986-994, (1996).
Hirschhorn et al., A comprehensive review of genetic association studies. Genetics in Medicine, 4(2): 45-61, 2002.
Imai, H., et al., Detection of HIV-1 RNA in Heparinized Plasma of hIV-1 Seropositive Individuals, J. Virol. Methods, 36:181-184, (1992).
International Search Report dated Jan. 12, 2010 in application PCT/US09/61691.
Ioannidis et al., Replication validity of genetic association studies. Nature Genetics, 29:306-309, 2001.
James et al., A unique clonal JAK2 mutation leading to constitutive signalling causes polycythaemia vera, Nature, 438:1144-1148 (2005).

(Continued)

*Primary Examiner* — Jeanine A Goldberg
(74) *Attorney, Agent, or Firm* — Foley & Lardner LLP

(57) ABSTRACT

The invention disclosed herein is based on the identification of novel mutations in the JAK2 gene and JAK2 protein. The invention provides compositions and methods useful for diagnosing hematopoietic diseases including, for example, myeloproliferative diseases. The invention also provides compositions and methods useful for determining a prognosis of an individual diagnosed as having a hematopoietic disease.

9 Claims, 6 Drawing Sheets

(56) References Cited

OTHER PUBLICATIONS

Jelinek et al., JAK2 mutation 1849G>T is rare in acute leukemias but can be found in CMML, Philadelphia chromosome-negative CML, and megakaryocytic leukemia, Blood, 106(10): 3370-3373, 2005.

Jilani et al., Better detection of FLT3 internal tandem duplication using peripheral blood plasma. Leukemia, 17:114-119, 2003.

Jones, et al., Widespread occurrence of the JAK2 V617F mutation in chronic myeloproliferative disorders, Blood, 106:2162-2168 (2005).

Kantarjian, H., et al., Quantitative Polymerase Chain Reaction Monitoring of BCR-ABL during Therapy With Imatinib Mesylate (ST1571; Gleevec) in Chronic-Phase Chronic Myelogenous Leukemia, Clin. Cancer Res. 9:160-6 (2003).

Karet, F. E., et al., Quantification of mRNA in Human Tissue Using Fluorescent Nested Reverse-Transcripterase Polymerase Chain Reaction, Analytical Biochemistry, 220:384-390, (1994).

Kaushansky, K., On the Molecular Origins of the Chronic Myeloproliferative Disorders: It All Makes Sense, Hematology (Am Soc Hematol Educ Program), 533-7 (2005).

Kievits, T. et al., "NASBA™ isothermal enzymatic in vitro nucleic acid amplification optimized for the diagnosis of HIV-1 infection" J Virological Methods 35:273-286, (1991).

Kralovics, et al., A Gain-of-Function Mutation of JAK2 in Myeloproliferative Disorders, New Eng. J. Med., 352(17):1779-1790 (2005).

Kratz et al., Mutational screen reveals a novel JAK2 mutation, L611S, in a child with acute lymphoblastic leukemia, Leukemia, 20:381-383, 2006.

Levine et al., Activating mutation in the tyrosine kinase JAK2 in polycythemia vera, essential thrombocythemia, and myeloid metaplasia with myelofibrosis, Cancer Cell, 7:387-397 (2005).

Li et al., Clonal heterogeneity in polycythemia vera patients with JAK2 exon12 and JAK2-V617F mutations, Blood, 111:3863-3866 (2008).

Luo et al., Mutation in the JAK kinase JH2 domain hyperactivates Drosophila and mammalian Jak-stat pathways. Molecular and Cellular Biology, 17(3): 1562-1571, 1997.

Ma et al, Plasma is more sensitive than cells for the detection of JAK2 mutations and homozygous/hemizygous state.

Maniatis et al., DNA Transfection by Electroporation, Molecular Cloning, A Laboratory Manual, 2d, pp. 16.54-16.55(1989).

Moore, R. E., et al., Design of PCR primers that detect only mRNA in the presence of DNA, Nucleic Acids Res. 18:1921, (1991).

Nastiuk et al., Common mutations in BRCA1 and BRCA2 do not contribute to early prostate cancer in Jewish men. Prostate, 40(3): 172-177, 1999.

Nelson, M.E., and Steensma, D.P., JAK2 V617F in myeloid disorders: What do we know now, and wherea re we headed? Leuk. Lymphoma, 47:177-194 (2006).

Peeters et al., Fusion of TEL, the ETS-variant gene 6 (ETV6) to the receptor-associated kinase JAK2 as a result of t(9; 12) in a lymphoid and t(9; 15; 12) in a myeloid leukemia, Blood, 90:2535-2540, 1997.

Rashtchian, A., Amplification of RNA, PCR Methods Applic., 4:S83-S91, (1994).

Rogers, et al., Relative increase in leukemia-specific DNA in peripheral blood plasma from patients with acute myeloid leukemia and myelodysplasia. Blood 103, 2799-2801 (2004).

Saharinen et al., Regulation of the Jak2 Tyrosine Kinase by Its Psuedokinase Domain, Mol Cell Biol, 20:3387-3395 (2000).

Schindler, C.W., JAK-STAT signaling in human disease, J. Clin Invest., 109:1133-1137 (2002).

Scott et al., JAK2 Exon 12 Mutations in Polycythemia Vera and Idiopathic Erythrocytosis, N Engl J Med, 356:459-468 (2007).

Staerk et al., JAK2, the JAK2 V617F mutant and cytokine receptors. JAK2, son mutant V617F, et les recepteurs de cytokines. Pathologie Biologie, 35: 88-91, 2007.

Steensma, D.P. et al., The JAK2 V617F activating tyrosine kinase mutation is an infrequent event in both "atypical" myeloproliferatiave disorders and myelodysplastic syndromes, Blood 106:1207-2109 (2005).

Stroun, M., et al., Neoplastic Characteristic of the DNA Found in the Plasma of Cancer Patients, Oncology, 46:318-322, (1989).

Sulong et al., The V617F mutation in Jak2 is not found in childhood acute lymphoblastic leukemia. B.J. of Haematology, 130: 964-965, 2005.

Tefferi and Gilliland, The JAK2V617F tyrosine Kinase Mutation in Myeloproliferative: Status Report and Immediate Implications for Disease Classification and Diagnosis, Mayo Clin. Proc., 80:947-958 (2005).

Tyagi, S. et al., Multicolor molecular beacons for allele discrimination, Nature Biotechnology 16:49-53 (1998).

Urdea, M. S., et al., "Direct and Quantitative Detection of HIV-1 RNA in human plasma with a branched DNA signal amplification assay" AIDS 7 (suppl 2):S11-S 14, (1993).

Urdea, M.S. et al., Branched DNA amplification for the sensitive, direct detection of human hepatitis viruses, Nucleic Acids Research Symposium Series 24:197-200, (1991).

Vainchenker and Constantinescu, A Unique Activating Mutation in JAK2 (V617F) Is at the Origin of Polycythemia Vera and Allows a New Classification of Myeloproliferative Diseases, Hematology (American Society of Hematology), 195-200 (2005).

Vandamme, A.M. et al., Detection of HIV-1 RNA in plasma and serum samples using the NASBA amplification system compared to RNA-PCR, J. Virological Methods, 52:121-132, (1995).

Wang, A. M. et al., Quantitation of mRNA by the polymerase chain reaction, Proc. Natl. Acad. Sci. USA, 86:9717-9721, (1989).

Wiedmann, et al., Ligase Chain Reaction (LCR)—Overview and Applications, PCR Methods Appl., 3:551-564, (1994).

Yip et al., The lack of association between JAK2 V617F mutation and myelodysplastic syndrome with or without myelofibrosis. Leukemia, 20:1165, 2006.

Zhao, et al., Identification of an Acquired JAK2 Mutation in Polycythemia Vera, J. Biol. Chem., 280(24):22788-22792 (2005).

Extended European Search Report dated Mar. 26, 2012 for EPO Patent Application No. 09824031.0.

Besses et al., JAK2 mutations at Exon 12 and 14 in polycythemia vera and idiopathic erythrocytosis: Incidence and correlation with clinical characteristics. Blood, ASH annual Meeting Abstracts, Abstract 2532, 2007.

Lee et al., Structural effects of clinically observed mutations in JAK2 exons 13-15: comparison with V617F and exon 12 mutations. BMC Structural Biology, 9:58, 1-14, 2009.

Ma et al., Mutation profile of JAK2 transcripts in patients with chronic myeloproliferative neoplasias. Journal of Molecular Diagnostics, 11(1): 49-53, 2009.

Smith and Fan, The saga of JAK2 mutations and translocations in hematologic disorders: pathogenesis, diagnostic and therapeutic prospects, and revised World Health Organization diagnostic criteria for myeloproliferative neoplasms. Human Pathology, 39:795-810, 2008.

Tefferi, JAK and MPL mutations in myeloid malignancies. Leukemia & Lymphoma, 49(3): 388-397, 2008.

Office Action issued by the Examiner in U.S. Appl. No. 12/503,318 on Aug. 28, 2012.

Dalal et al., "Cloning and Characterization of the Human Homolog of Mouse Jak2," Blood, vol. 91, pp. 844-851, 1998.

* cited by examiner

Series of Representative Sequencing Chromatograms

Exon 13 mutations

Exon 14 deletion

Exon 15 mutation

SEQUENCE LISTING

<160> NUMBER OF SEQ ID NOS: 11

<210> SEQ ID NO 1
<211> LENGTH: 5097
<212> TYPE: DNA
<213> ORGANISM: Homo sapiens

<400> SEQUENCE: 1

```
ctgcaggaag gagagaggaa gaggagcaga aggggcagc agcggacgcc gctaacggcc      60
tccctcggcg ctgacaggct gggccggcgc ccggctcgct tgggtgttcg cgtcgccact     120
tcggcttctc ggccggtcgg gcccctcggc ccgggcttgc ggcgcgcgtc ggggctgagg     180
gctgctgcgg cgcagggaga ggcctggtcc tcgctgccga gggatgtgag tgggagctga     240
gcccacactg gagggcccc gagggcccag cctggaggtc gttcagagcc gtgcccgccc      300
cggggcttcg cagaccttga cccgccgggt aggagccgcc cctgcgggct cgaggcgcg      360 ctctggtcgc ccgatctgtg tagccggttt cagaagcagg caacaggaac aagatgtgaa     420
ctgtttctct tctgcagaaa aagaggctct tcctcctcct cccgcgacgg caaatgttct     480
gaaaaagact ctgcatggga atggcctgcc ttacgatgac agaaatggag ggaacatcca     540
cctcttctat atatcagaat ggtgatattt ctggaaatgc caattctatg aagcaaatag     600
```

```
atccagttct tcaggtgtat ctttaccatt cccttgggaa atctgaggca gattatctga    660
cctttccatc tggggagtat gttgcagaag aaatctgtat tgctgcttct aaagcttgtg    720
gtatcacacc tgtgtatcat aatatgtttg ctttaatgag tgaaacagaa aggatctggt    780
atccacccaa ccatgtcttc catatagatg agtcaaccag gcataatgta ctctacagaa    840
taagatttta ctttcctcgt tggtattgca gtggcagcaa cagagcctat cggcatggaa    900
tatctcgagg tgctgaagct cctcttcttg atgactttgt catgtcttac ctctttgctc    960
agtggcggca tgattttgtg cacggatgga taaaagtacc tgtgactcat gaaacacagg   1020
aagaatgtct tgggatggca gtgttagata tgatgagaat agccaaagaa acgatcaaa    1080 ccccactggc catctataac tctatcagct acaagacatt cttaccaaaa tgtattcgag   1140
caaagatcca agactatcat attttgacaa ggaagcgaat aaggtacaga tttcgcagat   1200
ttattcagca attcagccaa tgcaaagcca ctgccagaaa cttgaaactt aagtatctta   1260
taaatctgga aactctgcag tctgccttct acacagagaa atttgaagta aaagaacctg   1320
gaagtggtcc ttcaggtgag gagattttg caaccattat aataactgga aacggtggaa    1380
ttcagtggtc aagagggaaa cataaagaaa gtgagacact gacagaacag gatttacagt   1440
tatattgcga ttttcctaat attattgatg tcagtattaa gcaagcaaac caagagggtt   1500
caaatgaaag ccgagttgta actatccata gcaagatgg taaaaatctg gaaattgaac    1560
ttagctcatt aagggaagct ttgtctttcg tgtcattaat tgatggatat tatagattaa   1620
ctgcagatgc acatcattac ctctgtaaag aagtagcacc tccagccgtg cttgaaaata   1680
tacaaagcaa ctgtcatggc ccaatttcga tggattttgc cattagtaaa ctgaagaaag   1740
caggtaatca gactggactg tatgtacttc gatgcagtcc taaggacttt aataaatatt   1800
ttttgacttt tgctgtcgag cgagaaaatg tcattgaata taaacactgt ttgattacaa   1860
aaaatgagaa tgaagagtac aacctcagtg ggacaaagaa gaacttcagc agtcttaaag   1920
atcttttgaa ttgttaccag atggaaactg ttcgctcaga caatataatt ttccagttta   1980
ctaaatgctg tcccccaaag ccaaaagata atcaaaccct tctagtcttc agaacgaatg   2040
gtgtttctga tgtaccaacc tcaccaacat tacagaggcc tactcatatg aaccaaatgg   2100
tgtttcacaa aatcagaaat gaagatttga tatttaatga agccttggcc caaggcactt   2160
ttacaaagat tttaaaggc gtacgaagag aagtaggaga ctacggtcaa ctgcatgaaa    2220
cagaagttct tttaaaagtt ctggataaag cacacagaaa ctattcagag tctttctttg   2280
aagcagcaag tatgatgagc aagctttctc acaagcattt ggttttaaat tatgagtat    2340 gtgtctgtgg agacgagaat attctggttc aggagtttgt aaaatttgga tcactagata   2400
catatctgaa aaagaataaa aattgtataa atatattatg gaacttgaa gttgctaaac    2460 agttggcatg ggccatgcat tttctagaag aaaacaccct tattcatggg aatgtatgtg   2520
ccaaaaatat tctgcttatc agaagaagag acaggaagac aggaaatcct cctttcatca   2580
aacttagtga tcctggcatt agtattacag ttttgccaaa ggacattctt caggagagaa   2640
taccatgggt accacctgaa tgcattgaaa tcctaaaaa tttaaatttg gcaacagaca    2700
aatggagttt tggtaccact ttgtgggaaa tctgcagtgg aggagataaa cctctaagtg   2760
ctctggattc tcaaagaaag ctacaatttt atgaagatag gcatcagctt cctgcaccaa   2820
agtgggcaga attagcaaac cttataaata attgtatgga ttatgaacca gatttcaggc   2880
cttctttcag agccatcata cgagatctta acagtttgtt tactccagat tatgaactat   2940
taacagaaaa tgacatgtta ccaaatatga ggataggtgc cctagggttt tctggtgcct   3000
```

```
ttgaagaccg ggatcctaca cagtttgaag agagacattt gaaatttcta cagcaacttg    3060
gcaagggtaa ttttgggagt gtggagatgt gccggtatga ccctctacag gacaacactg    3120
gggaggtggt cgctgtaaaa aagcttcagc atagtactga agagcaccta agagactttg    3180
aaagggaaat tgaaatcctg aaatccctac agcatgacaa cattgtaaag tacaagggag    3240
tgtgctacag tgctggtcgg cgtaatctaa aattaattat ggaatattta ccatatggaa    3300
gtttacgaga ctatcttcaa aaacataaag aacggataga tcacataaaa cttctgcagt    3360
acacatctca gatatgcaag ggtatggagt atcttggtac aaaaaggtat atccacaggg    3420
atctggcaac gagaaatata ttggtggaga acgagaacag agttaaaatt ggagattttg    3480
ggttaaccaa agtcttgcca caagacaaag aatactataa agtaaaagaa cctggtgaaa    3540
gtcccatatt ctggtatgct ccagaatcac tgacagagag caagtttttct gtggcctcag    3600 atgtttggag ctttggagtg gttctgtatg aacttttcac atacattgag aagagtaaaa    3660
gtccaccagc ggaatttatg cgtatgattg gcaatgacaa acaaggacag atgatcgtgt    3720
tccatttgat agaacttttg aagaataatg gaagattacc aagaccagat ggatgcccag    3780
atgagatcta tatgatcatg acagaatgct ggaacaataa tgtaaatcaa cgcccctcct    3840
ttagggatct agctcttcga gtggatcaaa taagggataa catggctgga tgaaagaaat    3900
gaccttcatt ctgagaccaa agtagattta cagaacaaag ttttatattt cacattgctg    3960
tggactatta ttacatatat cattattata taaatcatga tgctagccag caaagatgtg    4020
aaaatatctg ctcaaaactt tcaaagttta gtaagttttt cttcatgagg ccaccagtaa    4080
aagacattaa tgagaattcc ttagcaagga ttttgtaaga agtttcttaa acattgtctg    4140
ttaacatcac tcttgtctgg caaaagaaaa aaaatagact tttttcaactc agctttttga    4200 gacctgaaaa aattattatg taaattttgc aatgttaaag atgcacagaa tatgtatgta    4260 tagttttttac cacagtggat gtataatacc ttggcatctt gtgtgatgtt ttacacacat    4320
gagggctggt gttcattaat actgtttctt aattttttcca tagttaatct ataattaatt    4380
acttcactat acaaacaaat taagatgttc agataattga ataagtaacct ttgtgtcctt    4440 gttcatttat atcgctggcc agcattataa gcaggtgtat acttttagct tgtagttcca    4500
tgtactgtaa atatttttca cataaaggga acaaatgtct agttttatttt gtataggaaa    4560 tttccctgac cctaaataat acattttgaa atgaaacaag cttacaaaga tataatctat    4620
tttattatgg tttccccttgt atctatttgt ggtgaatgtg ttttttaaat ggaactatct    4680
ccaaattttt ctaagactac tatgaacagt tttcttttaa aattttgaga ttaagaatgc    4740
caggaatatt gtcatccttt gagctgctga ctgccaataa cattcttcga tctctgggat    4800
ttatgctcat gaactaaatt taagcttaag ccataaaata gattagattg tttttttaaaa    4860 atggatagct cattaagaag tgcagcaggt taagaatttt ttcctaaaga ctgtatattt    4920
gaggggtttc agaattttgc attgcagtca tagaagagat ttatttcctt tttagagggg    4980
aaatgaggta aataagtaaa aaagtatgct tgttaatttt attcaagaat gccagtagaa    5040
aattcataac gtgtatcttt aagaaaaatg agcatacatc ttaaatcttt tcaatta      5097
```

<210> SEQ ID NO 2
<211> LENGTH: 1132
<212> TYPE: PRT
<213> ORGANISM: Homo sapiens

<400> SEQUENCE: 2

Met Gly Met Ala Cys Leu Thr Met Thr Glu Met Glu Gly Thr Ser Thr
1               5                   10                  15

```
Ser Ser Ile Tyr Gln Asn Gly Asp Ile Ser Gly Asn Ala Asn Ser Met
        20                  25                  30

Lys Gln Ile Asp Pro Val Leu Gln Val Tyr Leu Tyr His Ser Leu Gly
            35                  40                  45

Lys Ser Glu Ala Asp Tyr Leu Thr Phe Pro Ser Gly Glu Tyr Val Ala
 50                  55                  60

Glu Glu Ile Cys Ile Ala Ala Ser Lys Ala Cys Gly Ile Thr Pro Val
 65                  70                  75                  80

Tyr His Asn Met Phe Ala Leu Met Ser Glu Thr Glu Arg Ile Trp Tyr
                 85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
            115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
            195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
            325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
```

```
              435                 440                 445
Tyr Lys His Cys Leu Ile Thr Lys Asn Glu Asn Glu Glu Tyr Asn Leu
                    450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
                    485                 490                 495
Lys Cys Cys Pro Pro Lys Pro Lys Asp Lys Ser Asn Leu Leu Val Phe
                500                 505                 510
Arg Thr Asn Gly Val Ser Asp Val Pro Thr Ser Pro Thr Leu Gln Arg
                515                 520                 525
Pro Thr His Met Asn Gln Met Val Phe His Lys Ile Arg Asn Glu Asp
                530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
                565                 570                 575
Glu Val Leu Leu Lys Val Leu Asp Lys Ala His Arg Asn Tyr Ser Glu
                580                 585                 590
Ser Phe Phe Glu Ala Ala Ser Met Met Ser Lys Leu Ser His Lys His
                595                 600                 605
Leu Val Leu Asn Tyr Gly Val Cys Val Cys Gly Asp Glu Asn Ile Leu
                610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
                    645                 650                 655
Leu Ala Trp Ala Met His Phe Leu Glu Glu Asn Thr Leu Ile His Gly
                660                 665                 670
Asn Val Cys Ala Lys Asn Ile Leu Leu Ile Arg Glu Glu Asp Arg Lys
                675                 680                 685
Thr Gly Asn Pro Pro Phe Ile Lys Leu Ser Asp Pro Gly Ile Ser Ile
690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                    725                 730                 735
Trp Ser Phe Gly Thr Thr Leu Trp Glu Ile Cys Ser Gly Gly Asp Lys
                740                 745                 750
Pro Leu Ser Ala Leu Asp Ser Gln Arg Lys Leu Gln Phe Tyr Glu Asp
                755                 760                 765
Arg His Gln Leu Pro Ala Pro Lys Trp Ala Glu Leu Ala Asn Leu Ile
                770                 775                 780
Asn Asn Cys Met Asp Tyr Glu Pro Asp Phe Arg Pro Ser Phe Arg Ala
785                 790                 795                 800
Ile Ile Arg Asp Leu Asn Ser Leu Phe Thr Pro Asp Tyr Glu Leu Leu
                    805                 810                 815
Thr Glu Asn Asp Met Leu Pro Asn Met Arg Ile Gly Ala Leu Gly Phe
                820                 825                 830
Ser Gly Ala Phe Glu Asp Arg Asp Pro Thr Gln Phe Glu Glu Arg His
                835                 840                 845
Leu Lys Phe Leu Gln Gln Leu Gly Lys Gly Asn Phe Gly Ser Val Glu
850                 855                 860
```

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
            885                 890                 895

Arg Glu Ile Glu Ile Leu Lys Ser Leu Gln His Asp Asn Ile Val Lys
        900                 905                 910

Tyr Lys Gly Val Cys Tyr Ser Ala Gly Arg Arg Asn Leu Lys Leu Ile
    915                 920                 925

Met Glu Tyr Leu Pro Tyr Gly Ser Leu Arg Asp Tyr Leu Gln Lys His
930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
            965                 970                 975

Leu Ala Thr Arg Asn Ile Leu Val Glu Asn Glu Asn Arg Val Lys Ile
        980                 985                 990

Gly Asp Phe Gly Leu Thr Lys Val Leu Pro Gln Asp Lys Glu Tyr Tyr
    995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 3
<211> LENGTH: 128
<212> TYPE: DNA
<213> ORGANISM: Homo sapiens

<400> SEQUENCE: 3
ataaatcaaa ccttctagtc ttcagaacga atggtgtttc tgatgtacca acctcaccaa      60
cattacagag gcctactcat atgaaccaaa tggtgtttca caaatcaga atgaagatt       120 tgatattt                                                              128

<210> SEQ ID NO 4
<211> LENGTH: 135
<212> TYPE: DNA
<213> ORGANISM: Homo sapiens

<400> SEQUENCE: 4
aatgaaagcc ttggccaagg cacttttaca aagattttta aaggcgtacg aagagaagta      60
ggagactacg gtcaactgca tgaaacagaa gttcttttaa aagttctgga taaagcacac     120

```
agaaactatt cagag                                                    135

<210> SEQ ID NO 5
<211> LENGTH: 88
<212> TYPE: DNA
<213> ORGANISM: Homo sapiens

<400> SEQUENCE: 5
tctttctttg aagcagcaag tatgatgagc aagctttctc acaagcattt ggttttaaat    60
tatggagtat gtgtctgtgg agacgaga                                      88

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtaaaacga cggccagtct aaatgctgtc ccccaaag                            38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caggaaacag ctatgacccc atgccaactg tttagcaa                            38

<210> SEQ ID NO 8
<211> LENGTH: 11
<212> TYPE: DNA
<213> ORGANISM: Homo sapiens

<400> SEQUENCE: 8
cgtackaaga g                                                        11

<210> SEQ ID NO 9
<211> LENGTH: 11
<212> TYPE: DNA
<213> ORGANISM: Homo sapiens

<400> SEQUENCE: 9
actacrgtca a                                                        11

<210> SEQ ID NO 10
<211> LENGTH: 39
<212> TYPE: DNA
<213> ORGANISM: Homo sapiens

<400> SEQUENCE: 10
aaactattca gagwywttct kkkwmrcrrs wwkkwwraw                           39

<210> SEQ ID NO 11
<211> LENGTH: 14
<212> TYPE: DNA
<213> ORGANISM: Homo sapiens

<400> SEQUENCE: 11
atattcyggt tcag                                                     14
```

COMPOSITIONS AND METHODS FOR DETECTING MUTATIONS IN JAK2 NUCLEIC ACID

CROSS-REFERENCE TO RELATED APPLICATIONS

This application is a continuation-in-part of PCT Application No. PCT/US2009/061691, filed Oct. 22, 2009 and U.S. application Ser. No. 12/503,318, filed Jul. 15, 2009, which claims benefit of U.S. Provisional Application No. 61/110,501, filed Oct. 31, 2008; each of which is hereby incorporated by reference in its entirety.

FIELD OF THE INVENTION

This invention relates to the field of disease detection and more specifically to compositions and diagnostic methods useful for patients having hematopoietic disorders such as a myeloproliferative disease.

BACKGROUND OF THE INVENTION

The following discussion of the background of the invention is merely provided to aid the reader in understanding the invention and is not admitted to describe or constitute prior art to the invention.

The Janus kinases are a family of tyrosine kinases that play a role in cytokine signaling. For example, JAK2 kinase acts as an intermediary between membrane-bound cytokine receptors such as the erythropoietin receptor (EpoR), and downstream members of the signal transduction pathway such as STAT5 (Signal Transducers and Activators of Transcription protein 5). See, e.g., Schindler, C. W., J. Clin Invest. 109: 1133-1137 (2002); Tefferi and Gilliland, Mayo Clin. Proc. 80:947-958 (2005); Giordancto and Kroemer, Protein Engineering, 15(9):727-737 (2002). JAK2 is activated when cytokine receptor/ligand complexes phosphorylate the associated JAK2 kinase, Id. JAK2 can then phosphorylate and activate its substrate molecule, for example STAT5, which enters the nucleus and interacts with other regulatory proteins to affect transcription. Id.; Nelson, M. E., and Steensma, D. P., Leuk. Lymphoma 47:177-194 (2006).

Certain hematopoietic diseases including non-CML myeloproliferative diseases (MPDs) such as polycythemia vera (PV), essential thrombocythemia (ET), and chronic idiopathic myelofibrosis (IMF) and as of yet unclassified myeloproliferative diseases (MPD-NC) are characterized by an aberrant increase in blood cells. See e.g., Vainchenker and Constantinescu. Hematology (American Society of Hematology), 195-200 (2005). This increase is generally initiated by a spontaneous mutation in a multipotent hematopoietic stem cell located in the bone marrow. Id. Due to the mutation, the stem cell produces far more blood cells of a particular lineage than normal, resulting in the overproduction of cells such as erythroid cells, megakaryocytes, granulocytes and monocytes. Some symptoms common to patients with MPD include enlarged spleen, enlarged liver, elevated white, red and/or platelet cell count, blood clots (thrombosis), weakness, dizziness and headache. Diseases such as PV, ET and IMF may presage leukemia, however the rate of transformation (e.g., to blast crisis) differs with each disease. Id. It has long been postulated that perturbation of protein tyrosine kinase (PTK) signaling by mutations and other genetic alterations is associated with MPDs. Mutant PTKs such as, for example, Janus kinase 2 (JAK2) gene mutations, can lead to constitutive activity in patients with MPDs.

The specific gene and concomitant mutation or mutations responsible for many MPDs is not known. However, a mutation in the Janus kinase 2 (JAK2) gene, a cytoplasmic, non-receptor tyrosine kinase, has been identified in a number of MPDs. The discovery of the JAK2 V617F mutation was a milestone in unveiling the molecular pathogenesis of MPDs. For example, this mutation has been reported in up to 97% of patients with PV, and in greater than 40% of patients with either ET or IMF. See e.g., Baxter et al., Lancet 365:1054-1060 (2005); James et al., Nature 438:1144-1148 (2005); Zhao, et al., J. Biol. Chem. 280(24):22788-22792 (2005); Levine et al., Cancer Cell, 7:387-397 (2005); Kralovics, et al., New Eng. J. Med. 352(17):1779-1790 (2005); Jones, et al., Blood 106:2162-2168 (2005); Steensma, et al., Blood 106: 1207-2109 (2005).

A variety of different approaches and a large body of evidence suggest that, when present, the JAK2 V617F mutation contributes to the pathogenesis of MPD. See e.g., Kaushansky, Hematology (Am Soc Hematol Educ Program), 533-7 (2005). The mutation has been detected from blood samples, bone marrow and buccal samples (see, e.g., Baxter et al., Lancet 365:1054-1060 (2005); James et al., Nature 438: 1144-1148 (2005); Zhao, et al., J. Biol. Chem. 280(24): 22788-22792 (2005); Levine et al., Cancer Cell, 7:387-397 (2005); Kralovics, et al., New Eng. J. Med. 352(17):1779-1790 (2005)), and homozygous and heterozygous cell populations have been reported in MPD patients. Baxter et al., Lancet 365:1054-1060 (2005).

The JAK2 V617F substitution, which is located in the pseudokinase domain of JAK2, relieves the auto-inhibition of its kinase activity, leading to a constitutively active kinase and augments downstream JAK2-STAT signaling pathways (see e.g., Saharinen et al., Mol Cell Biol 20:3387-3395 (2000); Saharinen et al., Mol. Biol Cell 14:1448-1459 (2003). Other JAK2 mutations in humans including translocations, point mutations, deletions, and insertions have been reported. See e.g., Scott et al., N Engl J Med 356:459-468 (2007); Li et al., Blood 111:3863-3866 (2008).

SUMMARY OF THE INVENTION

The invention is based on the identification of previously unknown mutations in the JAK2 gene and JAK2 protein. Specifically, the JAK2 gene and protein mutations include the mutations shown in Table 2. The invention further provides compositions and methods useful in the diagnosis and prognosis of hematopoietic diseases including, for example, myeloproliferative diseases.

In one aspect, the invention provides an isolated nucleic acid of at least 17 nucleotides of SEQ ID NO: 1, in which the fragment has a mutation selected from the mutations shown in Table 2, and the isolated nucleic acid is less than 5000 nucleotides. In one embodiment, the isolated nucleic acid includes at least one additional mutation shown in Table 2. In another embodiment, the isolated nucleic acid is labeled with a detectable label.

In a second aspect, the invention provides a polypeptide of at least 10 contiguous amino acids of SEQ ID NO: 2 in which the polypeptide has a mutation selected from the mutations shown in Table 2, and the polypeptide is less than 1100 amino acids. In one embodiment, the polypeptide includes at least one additional mutation shown in Table 2. In another embodiment, the fragment is labeled with a detectable label.

In another aspect, the invention provides a method for diagnosing a hematopoictic disease in an individual comprising: a) providing s sample from said individual, wherein said sample comprises JAK2 nucleic acid, b) evaluating a sample from the individual for the presence or absence of one or more mutations in JAK2 nucleic acid in which one or more mutations is selected from the group consisting of the mutations of Table 2, and c) identifying the individual as having a hematopoietic disease when the JAK2 nucleic acid comprises at least one of the mutations.

In another aspect, the invention provides a method of determining a prognosis of an individual diagnosed with a hematopoietic disease, the method comprising: (a) determining the presence or absence of one or more mutations in a JAK2 nucleic acid sample in which one or more mutations is selected from the group consisting of the mutations of Table 2; and (b) identifying the individual as having poor prognosis when one or more mutations are present in the JAK2 nucleic acid sample.

In another aspect, the invention provides a method for selecting therapy for an individual with a hematopoietic disorder comprising evaluating a sample containing nucleic acids from the individual for the presence or absence of one or more mutations in JAK2 nucleic acid in which one or more mutations is selected from the group consisting of the mutations shown in Table 2 and selecting the therapy based on mutations in JAK2 nucleic acid.

In some embodiments of any of the above aspects of the invention, the JAK2 nucleic acid is RNA. In other embodiments of any of the above aspects of the invention, the presence or absence of one or more mutations may be determined relative to SEQ ID NO: 1. In certain embodiments of any of the above aspects of the invention, the JAK2 nucleic acid includes two or more of the mutations shown in Table 2.

In still other embodiments of any of the above aspects of the invention, evaluating or determining the presence or absence of one or more mutations in a JAK2 nucleic acid sample includes amplifying JAK2 nucleic acid and hybridizing the amplified JAK2 nucleic acid with a detection oligonucleotide that is capable of specifically detecting a JAK2 nucleic acid mutant sequence under hybridization conditions. In other embodiments of any of the above aspects of the invention, evaluating or determining the presence or absence of one or more mutations in a JAK2 nucleic acid sample includes amplifying JAK2 nucleic acid and performing direct sequencing analysis of the amplified nucleic acid.

In another aspect, the invention provides a method for diagnosing a hematopoietic disease in an individual comprising: a) evaluating a sample containing polypeptides from the individual for the presence or absence of one or more mutations in JAK2 polypeptide in which one or more mutations is selected from the group consisting of the mutations of Table 2, and b) identifying the individual as having a hematopoietic disease when the JAK2 polypeptide comprises at least one of the mutations.

In another aspect, the invention provides a method of determining a prognosis of an individual diagnosed with a hematopoietic disease, the method comprising: (a) determining the presence or absence of one or more mutations in a JAK2 polypeptide sample in which one or more mutations is selected from the group consisting of the mutations of Table 2; and (b) identifying the individual as having poor prognosis when one or more mutations are present in the JAK2 polypeptide.

In one aspect, the invention provides a method for selecting therapy for an individual with a hematopoietic disorder comprising evaluating a sample containing polypeptides from the individual for the presence or absence of one or more mutations in JAK2 polypeptide in which one or more mutations is selected from the group consisting of the mutations shown in Table 2 and selecting the therapy based on mutations in JAK2 polypeptide.

In some embodiments of the above aspects of the invention, the presence or absence of one or more mutations may be determined relative to SEQ ID NO: 2. In certain embodiments of the above aspects, the JAK2 polypeptide includes 2 or more of the mutations shown in Table 2. In certain embodiments of the above aspects, evaluating a sample or determining the presence or absence of one or more mutations in a JAK2 polypeptide sample includes using an antibody that specifically binds to the mutated JAK2 polypeptide.

In some embodiments of any of the above aspects of the invention, the JAK2 nucleic acid and/or polypeptide sample is from a biological fluid from the patient, preferably the sample is blood, serum, or plasma.

In certain embodiments of any of the above aspects of the invention, the disease is a myeloproliferative disease; more preferably, the myeloproliferative disease is polycythemia vera, essential thrombocythemia, idiopathic myelofibrosis, or an unclassified myeloproliferative disease.

In another aspect, the invention provides a method for diagnosing a hematopoietic disease in an individual by: a) providing sample from said individual, wherein the sample comprises JAK2 nucleic acid; b) evaluating the JAK2 nucleic acid from the sample to determine whether the nucleotide sequence encoding exon 14 is deleted; and c) diagnosing the individual as having a hematopoietic disease when the nucleotide sequence exon 14 is identified as being deleted. In certain embodiments, the entire sequence of exon 14 is deleted (i.e., the nucleotide sequence corresponding to nucleotides 2271-2358 of SEQ ID NO: 1).

Any suitable method for evaluation may be used including, for example, amplifying all of the JAK2-encoding region of the nucleic acid, or a portion of the JAK2 nucleic acid which encodes exon 14. Desirably, such an amplification is performed using oligonucleotide primers which flank exon 14. Evaluation of the JAK2 nucleic acid for the deletion of exon 14 may be done by evaluating the length of the amplification products. In one embodiment, the amplification product is at least 88 nucleotides shorter than the amplification product produced from a JAK2 nucleic acid in containing an intact exon 14 coding sequence.

Optionally, the relative proportion of JAK2 nucleic acid containing the exon 14 deletion is determined and/or the presence or absence of at least one other mutation identified in Table 2 is evaluated. Additionally, the JAK2 nucleic acid is further assessed for the presence or absence of the V617F mutation.

The invention also provides a method for diagnosing a hematopoietic disease in an individual by: a) providing sample from the individual, wherein the sample comprises JAK2 protein; b) evaluating the JAK2 protein from the sample to determine whether the any of the amino acids encoded by exon 14 of the JAK2 nucleic acid are deleted; and c) diagnosing said individual as having a hematopoietic disease when any of the amino acids encoded by exon 14 of the JAK2 nucleic acid are identified as being deleted. Optionally, the JAK2 protein is evaluated to determine whether the C-terminus comprises the amino acids IFWFRSL which may be indicative of the deletion of exon 14. Isolation and evaluation of the JAK2 protein may be done by any suitable means and may include immunoprecipitation. Relatedly, the invention also provides an antibody (e.g., a monoclonal or a polyclonal antibody) that specifically binds to a protein comprising the amino acid sequence IFWFRSL.

The term "neoplastic disease" refers to a condition characterized by an abnormal growth of new cells such as a tumor. A neoplasm includes solid and non-solid tumor types such as a carcinoma, sarcoma, leukemia and the like. A neoplastic disease may be malignant or benign.

The term "myeloproliferative disease (MPD)" or "myeloproliferative disorder" is meant to include non-lymphoid dysplastic or neoplastic conditions arising from a hematopoietic stem cell or its progeny. "MPD patient" includes a patient who has been diagnosed with an MPD. "Myeloproliferative disease" is meant to encompass the specific, classified types of myeloproliferative diseases including polycythemia vera (PV), essential thrombocythemia (ET) and idiopathic myelofibrosis (IMF). Also included in the definition are hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, and systemic mastocytosis (SM). "Myeloproliferative disease" is also meant to encompass any unclassified myeloproliferative diseases (UMPD or MPD-NC).

As used herein the terms "diagnose" or "diagnosis" or "diagnosing" refer to distinguishing or identifying a disease, syndrome or condition or distinguishing or identifying a person having a particular disease, syndrome or condition.

"Determining a prognosis" as used herein refers to the process in which the course or outcome of a condition in a patient is predicted. The term "prognosis" does not refer to the ability to predict the course or outcome of a condition with 100% accuracy. Instead, the term refers to identifying an increased or decreased probability that a certain course or outcome will occur in a patient exhibiting a given condition/marker, when compared to those individuals not exhibiting the condition. The nature of the prognosis is dependent upon the specific disease and the condition/marker being assessed. For example, a prognosis may be expressed as the amount of time a patient can be expected to survive, the likelihood that the disease goes into remission, or to the amount of time the disease can be expected to remain in remission.

As used herein, the term "treatment," "treating," or "treat" refers to care by procedures or application that are intended to relieve illness or injury. Although it is preferred that treating a condition or disease such as a myeloproliferative disease will result in an improvement of the condition, the term treating as used herein does not indicate, imply, or require that the procedures or applications are at all successful in ameliorating symptoms associated with any particular condition. Treating a patient may result in adverse side effects or even a worsening of the condition which the treatment was intended to improve.

By "subject" is meant a human or any other animal which contains a JAK2 gene that can be amplified using the primers and methods described herein. A subject can be a patient, which refers to a human presenting to a medical provider for diagnosis or treatment of a disease. A human includes pre and post natal forms.

As used herein, the term "patient" refers to one who receives medical care, attention or treatment. As used herein, the term is meant to encompass a person diagnosed with a disease such as myeloproliferative disease as well as a person who may be symptomatic for a disease but who has not yet been diagnosed.

The term "sample" or "patient sample" is meant to include biological samples such as tissues and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin.

The term "nucleic acid" or "nucleic acid sequence" refers to an oligonucleotide, nucleotide or polynucleotide, and fragments or portions thereof, which may be single or double stranded, and represent the sense or antisense strand. A nucleic acid may include DNA or RNA, and may be of natural or synthetic origin. For example, a nucleic acid may include mRNA, genomic DNA or cDNA. Nucleic acid may include nucleic acid that has been amplified (e.g. using polymerase chain reaction). The convention "NTwt###NTmut" is used to indicate a mutation that results in the wild-type nucleotide NTwt at position ### in the nucleic acid being replaced with mutant NTmut.

For the JAK2 nucleic acid sequence, a "mutation" means a JAK2 nucleic acid sequence that includes at least one nucleic acid variation as compared to reference sequence GenBank accession number NM_004972 (SEQ ID NO: 1). A mutation in JAK2 nucleic acid may result in a change in the encoded polypeptide sequence or the mutation may be silent with respect to the encoded polypeptide sequence. A change in an amino acid sequence may be determined as compared to SEQ ID NO: 2, as a reference amino acid sequence.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in a single nucleotide in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele). Because direct sequencing of plasma or cell samples as routinely performed in clinical laboratories does not reliably distinguish between hemizygosity and homozygosity, in some embodiments, these classes are grouped. For example, samples in which no or a minimal amount of wild-type nucleic acid is detected are termed "hemizygous/homozygous mutant." In some embodiments, a "minimal amount" may be between about 1-2%. In other embodiments, a minimal amount may be between about 1-3%. In still other embodiments, a "minimal amount" may be less than 1%.

The term "substantially all" as used herein means at least about 60%, about 70%, about 80%, about 90%, about 95%, about 99%, or 100%.

"Substantially pure" as used herein in the context of nucleic acid represents at least 50%, at least 60%, at least 70%, at least 80%, at least 90%, at least 95% or at least 99% of the nucleic acid in a sample. The nucleic acid sample may exist in solution or as a dry preparation.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, a "fragment" means a polynucleotide that is at least about 15, 20, 25, 30, 35, 40, 45, 50, 75, 100, 200, 300, 400, 500, 1000 nucleotides or more in length.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

By "substantially complementary" is meant that two sequences that will specifically hybridize. The skilled artisan will understand that substantially complementary sequences need not hybridize along their entire length.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group in this position. Oligonucleotides also may include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, reverse transcription, PCR, or a combination thereof. The oligonucleotide may be modified. For example, the oligonucleotide may be labeled with an agent that produces a detectable signal (e.g., a fluorophore).

The term "detectable label" as used herein refers to a molecule or a compound or a group of molecules or a group of compounds associated with a nucleic acid or a polypeptide and is used to identify the nucleic acid or the polypeptide. In some cases, the detectable label may be detected directly. In other cases, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

By "antibody that specifically binds to the mutated JAK2 polypeptide" is meant that the antibody preferentially binds to mutated JAK2 polypeptide and not to the wild type JAK2 polypeptide. Preferential binding of the antibody is meant to include at least 90% of the times the antibody will bind to mutated JAK2 polypeptide and discriminate between mutated and wild type JAK2 polypeptides.

As used herein, the term "activation domain" in reference to JAK2 refers generally to a domain involved in cell activation such as, for example, cell proliferation. An example of an activation domain is a kinase or pseudokinase domain.

As used herein, the term "pseudokinase domain" refers to a portion of a polypeptide or nucleic acid that encodes a portion of the polypeptide, where the portion shows homology to a functional kinase but possesses no catalytic activity. A pseudokinase domain may also be referred to as a "kinase-like domain." An example of a pseudokinase domain is the JAK2 pseudokinase domain, also termed the JH2 domain. The N-terminal part of JAK2 pseudokinase domain (JH2) is a regulatory domain that negatively regulates the activity of JAK2.

The term "kinase domain" refers to a portion of a polypeptide or nucleic acid that encodes a portion of the polypeptide, where the portion is required for kinase activity of the polypeptide (e.g., tyrosine kinase activity).

In some methods of the invention, mutations may "affect JAK2 kinase activity." The affected JAK2 kinase activity may include kinase activity that increases, decreases, becomes constitutive, stops completely or affects greater, fewer or different targets. A mutation that affects kinase activity may be present in a kinase domain or in a domain associated with a kinase domain such as the JAK2 pseudokinase domain.

As used herein, the term "including" has the same meaning as the term comprising.

DETAILED DESCRIPTION OF THE INVENTION

Figure 1A:
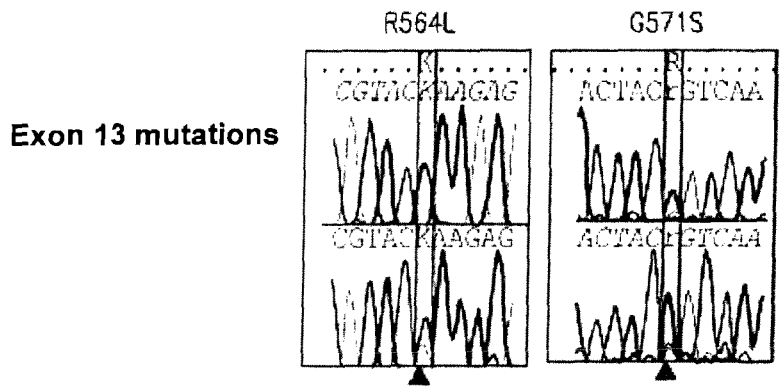
FIG. 1 is a series of representative sequencing chromatograms of Exon 13 mutations (FIG. 1A), Exon 14 deletion (FIG. 1B), and Exon 15 mutation (FIG. 1C). Arrows indicate positions of mutant nucleotides and dots indicate deleted nucleotides.
Figure 1B:
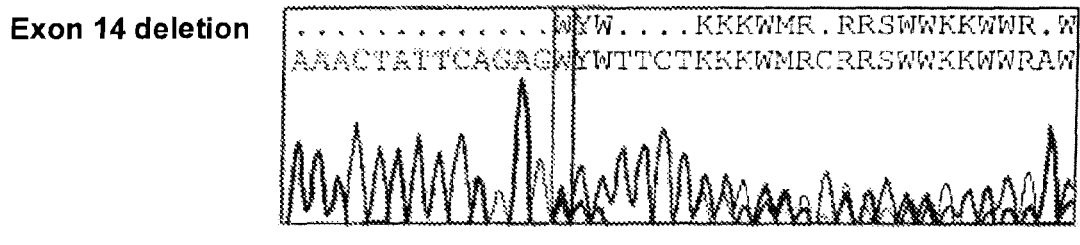
Figure 1C:
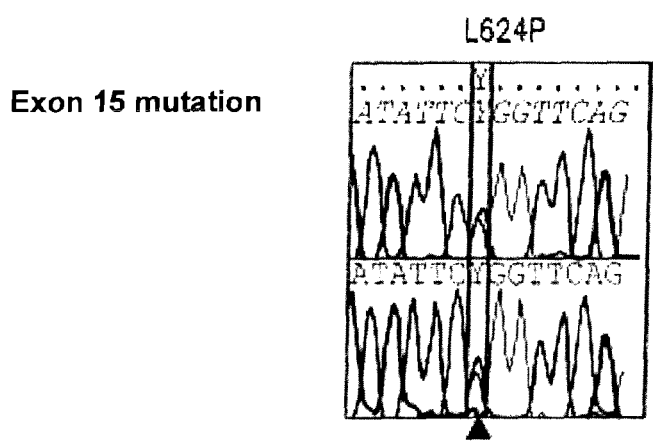
Figure 2:
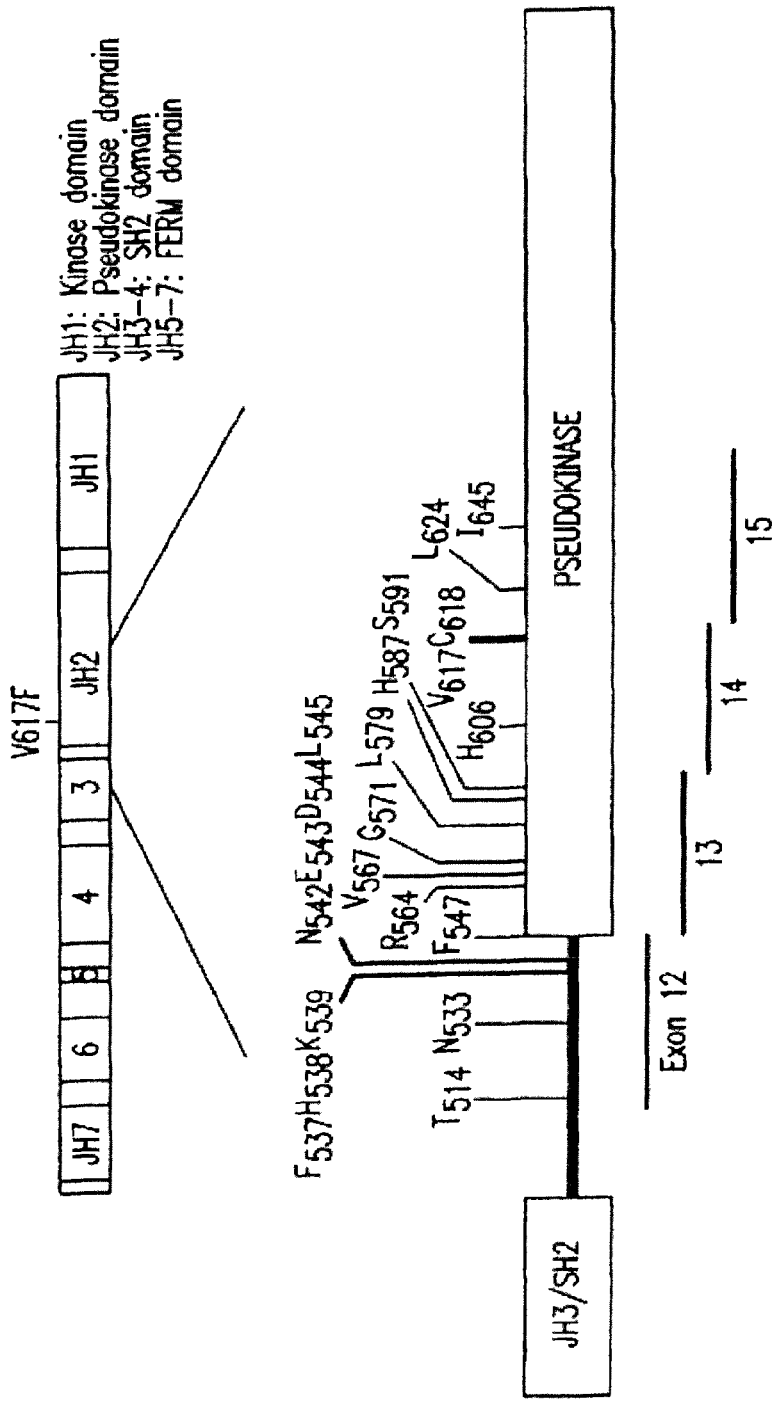
FIG. 2 is a schematic diagram of the JAK2 gene structure with some of the mutated residues in exons 12-15 shown.

The present invention is based on the discovery of previously unknown mutations in the JAK2 nucleic acid and protein which have been associated with myeloproliferative diseases. The mutations are shown in Table 2.

JAK2 Nucleic Acid

JAK2 genomic nucleic acid is located in human chromosome 9. Exemplary sequences of human JAK2 genomic sequences include but are not limited to GenBank Accession numbers: NG_009904, CM000260, CM000671, GL000069. These sequences are incorporated herein by reference.

Exemplary sequences of all or portions of human JAK2 mRNA include but are not limited to GenBank Accession numbers: NM_004972, human JAK2 mRNA. These sequences are incorporated herein by reference. Exemplary sequence of JAK2 mRNA is provided in SEQ ID NO: 1.

The JAK2 nucleic acids of this invention include, for example, nucleic acids that are substantially identical to a portion of the JAK2 nucleotide sequence of SEQ ID NO: 1 and further comprise one or more of the following mutations listed in Table 2. In some embodiments, the JAK2 nucleic acids have at least 10, 12, 14, 16, 18, 20, 25, 30, 40, 50, 75, 100, or more nucleotides in length. In some other embodiments, the JAK2 nucleic acids are less than 6000, 5000, 4000, 3000, 2000, 1000, 750, 500, 400, 300, or 200 nucleotides in length.

Biological Sample Collection and Preparation

The methods and compositions of this invention may be used to detect mutations in the JAK2 gene and/or JAK2 protein using a biological sample obtained from an individual. The nucleic acid (DNA or RNA) may be isolated from the sample according to any methods well known to those of skill in the art. If necessary the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the individual's cells to detect using polymerase chain reaction. Alternatively, mutations in the JAK2 gene may be detected using an acellular bodily fluid according to the methods described in U.S. patent application Ser. No. 11/408,241 (Publication No. US 2007-0248961), hereby incorporated by reference.

Plasma or Serum Preparation Methods

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70 degrees centigrade until thawed and used. "Fresh" plasma or serum should be refrigerated or maintained on ice until used, with nucleic acid (e.g., RNA, DNA or total nucleic acid) extraction being performed as soon as possible. Exemplary methods are described below.

Nucleic Acid Extraction and Amplification

The nucleic acid to be amplified may be from a biological sample such as an organism, cell culture, tissue sample, and the like. The biological sample can be from a subject which includes any animal, preferably a mammal. A preferred subject is a human, which may be a patient presenting to a medical provider for diagnosis or treatment of a disease. The biological sample may be obtained from a stage of life such as a fetus, young adult, adult, and the like. Particularly preferred subjects are humans being tested for the existence of a JAK2 mutation.

Various methods of extraction are suitable for isolating the DNA or RNA. Suitable methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France). In other methods, mRNA may be extracted from patient blood/bone marrow samples using MagNA Pure LC mRNA HS kit and Mag NA Pure LC Instrument (Roche Diagnostics Corporation, Roche Applied Science, Indianapolis, Ind.).

Numerous methods are known in the art for isolating total nucleic acid, DNA and RNA from blood, serum, plasma and bone marrow or other hematopoietic tissues. In fact, numerous published protocols, as well as commercial kits and systems are available. By way of example but not by way of limitation, examples of such kits, systems and published protocols are described below. Commercially available kits include Qiagen products such as the QiaAmp DNA Blood MiniKit (Cat. #51104, Qiagen, Valencia, Calif.), the QiaAmp RNA Blood MiniKit (Cat. #52304, Qiagen, Valencia, Calif.); Promega products such as the Wizard Genomic DNA Kit (Cat. #A1620, Promega Corp. Madison, Wis.), Wizard SV Genomic DNA Kit (Cat. #A2360, Promega Corp. Madison, Wis.), the SV Total RNA Kit (Cat. #X3100, Promega Corp. Madison, Wis.), PolyATract System (Cat. #Z5420, Promega Corp. Madison, Wis.), or the PurYield RNA System (Cat. #Z3740, Promega Corp. Madison, Wis.).

Extraction of RNA from Plasma or Serum

Plasma RNA is highly sensitive and may replace DNA-based testing because of the relative abundance of the RNA and the ease in detecting deletions such as, for example, deletion of Exon 14. Circulating extracellular deoxyribonucleic acid (DNA), including tumor-derived or associated extracellular DNA, is also present in plasma and serum. See Stroun, M., et al., Oncology 46:318-322, (1989). Since this DNA will additionally be extracted to varying degrees during the RNA extraction methods described above, it may be desirable or necessary (depending upon clinical objectives) to further purify the RNA extract and remove trace DNA prior to proceeding to further RNA analysis. This may be accomplished using DNase, for example by the method as described by Rashtchian, A., PCR Methods Applic. 4:S83-S91, (1994), as follows.

Glass beads, Silica particles or Diatom Extraction: RNA may be extracted from plasma or serum using silica particles, glass beads, or diatoms, as in the method or adaptations of Boom, R., et al., J. Clin. Micro. 28:495-503, (1990); Cheung, R. C., et al., J. Clin Micro. 32:2593-2597, (1994).

Acid Guanidinium Thiocyanate-Phenol-Chloroform Extraction: As an alternative method, RNA may be extracted from plasma or serum using the Acid Guanidinium Thiocyanate-Phenol-chloroform extraction method described by Chomczynski, P. and Sacchi, N., Analytical Biochemistry 162:156-159. (1987), as follows.

Alternative Nucleic Acid Extraction Methods: Alternative methods may be used to extract RNA from body fluids including but not limited to centrifugation through a cesium chloride gradient, including the method as described by Chirgwin, J. M., et al., Biochemistry 18:5294-5299, (1979), and co-precipitation of extracellular RNA from plasma or serum with gelatin, such as by adaptations of the method of Fournie, G. J., et al., Analytical Biochemistry 158:250-256, (1986), to RNA extraction.

Alternative Nucleic Acid Amplification Methods

Alternative methods of nucleic acid amplification which may be used include variations of RT-PCR, including quantitative RT-PCR, for example as adapted to the method described by Wang, A. M. et al., Proc. Natl. Acad. Sci. USA 86:9717-9721, (1989), or by Karet, F. E., et al., Analytical Biochemistry 220:384-390, (1994). Another method of nucleic acid amplification or mutation detection which may be used is ligase chain reaction (LCR), as described by Wiedmann, et al., PCR Methods Appl. 3:551-564, (1994). An alternative method of amplification or mutation detection is allele specific PCR (ASPCR). ASPCR which utilizes matching or mismatching between the template and the 3' end base of a primer well known in the art. See e.g., U.S. Pat. No. 5,639,611.

Another method of mutation detection is nucleic acid sequencing. Sequencing can be performed using any number of methods, kits or systems known in the art. One example is using dye terminator chemistry and an ABI sequencer (Applied Biosystems, Foster City, Calif.). Sequencing also may involve single base determination methods such as single nucleotide primer extension ("SNaPshot®" sequencing method) or allele or mutation specific PCR. The SNaPshot® Multiplex System is a primer extension-based method that enables multiplexing up to 10 SNPs (single nucleotide polymorphisms). The chemistry is based on the dideoxy single-base extension of an unlabeled oligonucleotide primer (or primers). Each primer binds to a complementary template in the presence of fluorescently labeled ddNTPs and AmpliTaq® DNA Polymerase, FS. The polymerase extends the primer by one nucleotide, adding a single ddNTP to its 3' end. SNaPshot® Multiplex System is commercially available (ABI PRISM® SNaPshot® Multiplex kit, Applied Biosystems Foster City, Calif.). Products generated using the ABI PRISM® SNaPshot® Multiplex kit can be analyzed with GeneScan® Analysis Software version 3.1 or higher using ABI PRISM®310 Genetic Analyzer, ABI PRISM® 3100 Genetic Analyzer or ABI PRISM® 3700 DNA Analyzer.

Exemplary Methods for Detection of JAK2 DNA and RNA Mutations

Nucleic acid (e.g., total nucleic acid) may be extracted from patient's biological sample using any appropriate method. Next, an RT-PCR reaction may be performed using either the total nucleic acid preparation or the RNA preparation to specifically amplify a portion of the patient RNA. An exemplary one-step RT-PCR system is the Superscript III System (Invitrogen, Carlsbad, Calif.). Other methods and systems for RT-PCR reactions are well known in the art and are commercially available. By way of example, but not by way of limitation, a primer pair for JAK2 may be 5'-TGT AAA ACG ACG GCC AGT CTA AAT GCT GTC CCC CAA AG-3' (forward primer, SEQ ID NO: 6) and 5'-CAG GAA ACA GCT ATG ACC CCA TGC CAA CTG TTT AGC AA-3' (reverse primer, SEQ ID NO: 7). The RT-PCR product may then be purified, for example by gel purification, and the resulting purified product may be sequenced. Nucleic acid sequencing methods are known in the art; an exemplary sequencing method includes the ART Prism BigDye Terminator v3.1 Cycle Sequencing Kit (Applied Biosystems, Foster City, Calif.). The sequencing data may then be analyzed for the presence or absence of one or more mutations in JAK2 nucleic acid. The sequencing data may also be analyzed to determine the proportion of wild-type to mutant nucleic acid present in the sample.

The presence or absence of JAK2 mutations can be determined in a nucleic acid by sequencing appropriate portions of the JAK2 gene containing the mutations sought to be detected. For example, each amplicon of the JAK2 gene is sequenced with forward and reverse primers. In another approach, JAK2 mutations that change susceptibility to digestion by one or more endonuclease restriction enzymes may be used to detect the mutations. In another embodiment, the presence of one or more JAK2 mutations can be determined by allele specific amplification. In yet another embodiment, the presence of one or more JAK2 mutations can be determined by primer extension. In yet a further embodiment, the presence of one or more JAK2 mutations can be determined by oligonucleotide ligation. In another embodiment, the presence of one or more JAK2 mutations can be determined by hybridization with a detectably labeled probe containing the mutant JAK2 sequence. The presence or absence of JAK2 mutations can be determined by any known or future method.

Detection of Mutated JAK2 Proteins

According to the invention, the presence or absence of JAK2 mutations can also be determined by analyzing the JAK2 protein (SEQ ID NO: 2) encoded by the mutated JAK2 gene. The mutations include those shown in Table 2. Detection of JAK2 mutations at the protein level can be detected by any method well known in the field. In one embodiment, detection of JAK2 mutations is carried out by isolating JAK2 protein and subjecting it to amino acid sequence determination. This may require fragmenting the protein by proteolytic or chemical means prior to sequencing. Methods of determining an amino acid sequence are well known in the art.

Detection of mutated JAK2 proteins can be accomplished using, for example, antibodies, aptamers, ligands/substrates, other proteins or protein fragments, other protein-binding agents, or mass spectrometry analysis of fragments. Preferably, protein detection agents are specific for the mutated JAK2 protein of the present invention and can therefore discriminate between a mutated protein and the wild-type protein or another variant form. This can generally be accomplished by, for example, selecting or designing detection agents that bind to the region of a protein that differs between the variant and wild-type protein.

One preferred agent for detecting a mutated JAK2 protein is an antibody capable of selectively binding to a variant form of the protein. Antibodies capable of distinguishing between wild-type and mutated JAK2 protein may be created by any suitable method known in the art. The antibodies may be monoclonal or polyclonal antibodies, single chain or double chain, chimeric or humanized antibodies or portions of immunoglobulin molecules containing the portions known in the state of the art to correspond to the antigen binding fragments.

Methods for manufacturing polyclonal antibodies are well known in the art. Typically, antibodies are created by administering (e.g., via subcutaneous injection) the mutated JAK2 protein immunogenic fragment containing the mutation to white New Zealand rabbits. The JAK2 antigen is typically injected at multiple sites and the injections are repeated multiple times (e.g., approximately bi-weekly) to induce an immune response. Desirably, the rabbits are simultaneously administered an adjuvant to enhance anti-JAK2 immunity. The polyclonal antibodies are then purified from a serum sample, for example, by affinity chromatography using the same JAK2 antigen to capture the antibodies. The antibodies can be made specific to the mutation by removing antibodies cross-reacting with native JAK2.

In vitro methods for detection of the mutated JAK2 proteins also include, for example, enzyme linked immunosorbent assays (ELISAs), radioimmunoassays (RIA), Western blots, immunoprecipitations, immunofluorescence, and protein arrays/chips (e.g., arrays of antibodies or aptamers). For further information regarding immunoassays and related protein detection methods, see Current Protocols in Immunology, John Wiley & Sons, N.Y., and Hage, "Immunoassays", Anal Chem. 1999 Jun. 15; 71(12):294R-304R. Additional analytic methods of detecting amino acid variants include, but are not limited to, altered electrophoretic mobility (e.g., 2-dimensional electrophoresis), altered tryptic peptide digest, altered JAK2 kinase activity in cell-based or cell-free assay, alteration in ligand or antibody-binding pattern, altered isoelectric point, and direct amino acid sequencing.

Diagnostic Tools

JAK2 nucleic acid may be used as tools to diagnose an individual as having (or as likely to develop) a myeloproliferative disease. Alternatively, the JAK2 mutation status, used alone or in combination with other clinical parameters, also may be used to determine a prognosis for a patient diagnosed as having a myeloproliferative disease. Exemplary mutations in JAK2 nucleic acid is listed in Tables 1 and 2.

In some embodiments, the JAK2 nucleic acids further comprise a detectable label and are used as a probe ("JAK2 probe") to detect mutated JAK2 nucleic acids in a patient sample. The JAK2 probe may be detectably labeled by methods known in the art. Useful labels include, for example, fluorescent dyes (e.g., Cy5®, Cy3®, FITC, rhodamine, lanthamide phosphors, Texas red, FAM, JOE, Cal Fluor Red 610®, Quasar 670®), radioisotopes (e.g., $^{32}P$, $^{35}S$, $^{3}H$, $^{14}C$, $^{125}I$, $^{131}I$), electron-dense reagents (e.g., gold), enzymes (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

In other embodiments, the JAK2 probes are TaqMan® probes, molecular beacons, and Scorpions (e.g., Scorpion™ probes). These types of probes are based on the principle of fluorescence quenching and involve a donor fluorophore and a quenching moiety. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to he an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes. Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), and the ATTO-series of quenchers (ATTO 540Q, ATTO 580Q, and ATTO 612Q; Atto-Tec GmbH).

With Scorpion primers, sequence-specific priming and PCR product detection is achieved using a single molecule. The Scorpion primer maintains a stem-loop configuration in the unhybridized state. The fluorophore is attached to the 5' end and is quenched by a moiety coupled to the 3' end, although in suitable embodiments, this arrangement may be switched The 3' portion of the stem also contains sequence that is complementary to the extension product of the primer. This sequence is linked to the 5' end of a specific primer via a non-amplifiable monomer. After extension of the primer moiety, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion primer, resulting in an extension product. A fluorescent signal is generated due to the separation of the fluorophore from the quencher resulting from the binding of the probe element (e.g., the JAK2 probe) of the Scorpion primer to the extension product.

TaqMan® probes (Heid, et al., Genome Res 6: 986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

The JAK2 polypeptides of this invention include, for example, polypeptides that are substantially identical to a portion of the JAK2 amino acid sequence of SEQ ID NO: 2 and further comprise one or more of the following mutations listed in Table 2. These polypeptides may be used as tools to diagnose an individual as having (or as likely to develop) a myeloproliferative disease. Alternatively, the JAK2 mutation status, used alone or in combination with other clinical parameters, also may be used to determine a prognosis for a patient diagnosed as having a myeloproliferative disease. In some embodiments, the JAK2 polypeptides have at least 10, 12, 14, 16, 18, 20, 25, 30, 40, 50, 75, 100, or more amino acids. In some embodiments, the JAK2 polypeptide is less than 1100, 1000, 900, 800, 700, 600, 500, or 400 amino acids.

Kits for Detecting JAK2 Mutations

The invention also provides kits for detecting JAK2 mutations. The kits will contain at least a primer pair capable of amplifying a target JAK2 nucleic acid sequence of SEQ ID NO: 1 and a means for detecting a JAK2 mutation in the target. Preferably, the amplification using the primer pair of the kit results in a reaction product having at least 20, 40, 60, 80, 100, 125, 150, 200, 300, 500, or more nucleotides. Suitable primer pairs include, for example, primers having the sequence of SEQ ID NOs: 6 and 7. Suitable means for detecting a JAK2 mutation in the reaction product make use of a detectably labeled JAK2 probe, such as those described herein.

Diagnosis, Detection, and Prognosis

The presence of the JAK2 mutations, such as, for example, the mutations listed in Table 2 alone, in combination with each other, or in combination with other JAK2 mutations can be as an indicator of disease.

Without wishing to be bound by any theory, it is believed that the JAK2 mutations allow the activation loop of the kinase domain to move away from the pseudokinase domain, thus leading to constitutive activation of the JAK2-STAT pathway. Mutations in the pseudokinase domain are expected to inactivate the auto-inhibitory function of the pseudokinase domain on the kinase activity. A considerable portion of activating mutations in tyrosine kinases associated with human cancer are loss-of-function alleles residing in the auto-inhibitory domains, for example, point mutations and deletions that result in constitutive tyrosine kinase activation. Therefore, testing for JAK2 mutations should include most of the pseudokinase domain.

Without wishing to be bound by any theory, it has been suggested from homology modeling approaches that residues 537 through 543 (mutation hot spots in exon 12) lie within a loop region bridging the SH2 and JH2 domains of JAK2. In the predicted model, positive polar or hydrophobic interactions between D407-K655, S411-E653, K415-E685, and F408-H608 from the SH2 and the JH2 domains, respectively, are closely packed in the predicted interface that further supported the JH2-JH1 interaction (21). Therefore, mutations in this loop area may disrupt JH2-JH1 interaction leading to constitutive kinase activation, e.g., del/F537-K539ins/L, del/N542-E543, H538QK539L and K539L, all displayed increased JAK2 activation, cytokine-independent hypersensitive proliferation, and in the case of K539L, developed a myeloproliferative phenotype. See e.g., Scott et al., N Engl J Med 356:459-468 (2007).

One or more of the following determinations may be used to diagnose a patient: determining the presence or absence of a specific JAK2 mutation, determining the zygosity status of the sample, and determining the ratio of mutant to wild-type JAK2 nucleic acid or mRNA in the sample. For example, patients found to carry a specific JAK2 mutation by the methods of the invention may be recommended for further testing to verify an MPD diagnosis, or detection of the mutation may be used to finally confirm a preliminary diagnosis of MPD (e.g., if a patient is symptomatic for an MPD and also tests positive for a specific JAK2 mutation known to be indicative of a particular MPD, the patient may be finally diagnosed with an MPD such as PV). Similarly, methods of the invention may be used to diagnose patients who are asymptomatic for MPD, for example patients who are in the very early stages of an MPD. JAK2 mutations may also be detected in MPD patients who are undergoing treatment; if the ratio of mutant to wild-type JAK2 nucleic acid or the zygosity status of the sample changes during treatment, a different diagnosis may be made.

One or more of the following determinations may be used to treat a patient: determining the presence or absence of a specific JAK2 mutation, determining the zygosity status of the sample, and determining the ratio of mutant to wild-type JAK2 nucleic acid in a sample. A physician or treatment specialist may administer, forego or alter a treatment or treatment regime based on one or more of the determinations. Further, the number of cancerous cells carrying the mutation may change during the course of an MPD and monitoring the ratio, the zygosity status, and/or the presence or absence of a JAK2 mutation may be an indication of disease status or treatment efficacy. For example, treatment may reduce the number of mutant cancerous cells, or the disease may become worse with time, and the number of diseased cells may increase. Additionally, one or more of the determinations may aid in patient prognosis and quality of life decisions. For example, decisions about whether to continue—or for how long to continue—a painful, debilitating treatment such as chemotherapy may be made.

The zygosity status and the ratio of wild-type to mutant nucleic acid in a sample may be determined by methods known in the art including sequence-specific, quantitative detection methods. Other methods may involve determining the area under the curves of the sequencing peaks from standard sequencing electropherograms, such as those created using ABI Sequencing Systems, (Applied Biosystems, Foster City Calif.). For example, the presence of only a single peak such as a "G" on an electropherogram in a position representative of a particular nucleotide is an indication that the nucleic acids in the sample contain only one nucleotide at that position, the "G." The sample may then be categorized as homozygous because only one allele is detected. The presence of two peaks, for example, a "G" peak and a "T" peak in the same position on the electropherogram indicates that the sample contains two species of nucleic acids; one species carries the "G" at the nucleotide position in question, the other carries the "T" at the nucleotide position in question. The sample may then be categorized as heterozygous because more than one allele is detected.

The sizes of the two peaks may be determined (e.g., by determining the area under each curve), and a ratio of the two different nucleic acid species may be calculated. A ratio of wild-type to mutant nucleic acid may be used to monitor disease progression, determine treatment, or to make a diagnosis. For example, the number of cancerous cells carrying a specific JAK2 mutation may change during the course of an MPD. If a base line ratio is established early in the disease, a later determined higher ratio of mutant nucleic acid relative to wild-type nucleic acid may be an indication that the disease is becoming worse or a treatment is ineffective; the number of cells carrying the mutation may be increasing in the patient. A lower ratio of mutant relative to wild-type nucleic acid may be an indication that a treatment is working or that the disease is not progressing; the number of cells carrying the mutation may be decreasing in the patient.

EXAMPLES

EXAMPLE 1

Detection of the JAK2 Mutations

Approximately 20,000 patient samples with suspicious diagnosis of MPD over a period of 7 months (from November, 2007 through June, 2008) were collected and screened for JAK2 gene mutation through the region of entire exons 12-15. Five milliliters of blood in Lavender (purple top tubes) containing ethylenediaminetetraacetic acid (EDTA) anticoagulant were required for analysis. Blood samples were refrigerated (not frozen) or kept at room temperature no more than 48 hr if immediate nucleic acid extraction was not possible.

Total nucleic acids were isolated from peripheral blood plasma by the NucliSens extraction kit (bioMerieux Inc., Durham, N.C., USA) according to the manufacturer's instructions. First strand cDNAs were then prepared by reverse transcription of total RNAs with random primers at 55° C. for 30 min, followed by PCR reactions using SuperSript III one-step RT-PCR system with Platinum Taq DNA polymerase (Invitrogen, Carlsbad, Calif., USA). For amplification of the JAK2 exons 12-15, the following primer set and conditions were used: 5'-TGT AAA ACG ACG GCC AGT CTA AAT GCT GTC CCC CAA AG-3' (forward primer, SEQ ID NO: 6) and 5'-CAG GAA ACA GCT ATG ACC CCA TGC CAA CTG TTT AGC AA-3' (reverse primer, SEQ ID NO: 7); initial step of 2 min at 94° C., followed by 40 cycles of 94° C. for 15 sec, 60° C. for 30 sec, and 68° C. for 1 min, and ending with one step of 68° C. for 7 min. The 491-bp amplified products were filter-purified by Multiscreen PCR plates (Millipore, Billerica, Mass., USA) and sequenced in both directions using the ABI Prism BigDye® Terminator v3.1 Cycle Sequencing Kit and detected by ABI PRISM 3100 Genetic Analyzer (Applied Biosystems, Foster City, Calif., USA). Sequence data was then base-called, assembled and analyzed by ABI Prism® SeqScape software (Applied Biosystems, Foster City, Calif., USA) using the JAK2 sequence (accession number NM004972) as a reference.

Table 1 presents a mutation analysis of JAK2 gene exon 12 (SEQ ID NO: 3), exon 13 (SEQ ID NO: 4), exon 14 (SEQ ID NO: 5), and exon 15 from a large group of suspected MPD blood samples.

TABLE 1

Mutation Analysis

| Exon* | Mutation | Codon change | No. of cases | Pattern on sequencing# |
|---|---|---|---|---|
| 12 | Silent | H531 | 1 | Heterozygous |
| 12 | Duplication | dupl/V536-F547 | 2 | Heterozygous |
| 12 | Deletion | del H538 | 1 | Heterozygous |
| 12 | Deletion | del/H538-K539 | 1 | Heterozygous |
| 12 | Deletion | del/N542-E543 | 5 | Heterozygous |
| 12 | Deletion | del/E543-D544 | 3 | Heterozygous |
| 12 | Indels | del/F537-K539 ins/K | 1 | Heterozygous |
| 12 | Indels | del/F537-K539 ins/L | 2 | Heterozygous |
| 12 | Indels | del/H538-K539 ins/L | 4 | Heterozygous |
| 12 | Indels | del/R541-E543 ins/K | 1 | Heterozygous |
| 12 | Indels | del/I540-D544 ins/MK | 1 | Heterozygous |
| 12 | Indels | del/N542-D544 ins/N | 1 | Heterozygous |
| 12 | Missense | T514M | 2 | Heterozygous |
| 12 | Missense | N533Y | 1 | Heterozygous |
| 12 | Missense | K539L | 2 | Heterozygous |
| 12 | Missense | H538Q K539L | 1 | Heterozygous |
| 12 | Missense | K539L L545V | 1 | Heterozygous |
| 12 | Missense | F547L | 1 | Heterozygous |
| 13 | Silent | G562 | 2 | Heterozygous |
| 13 | Silent | Y570 | 4 | Heterozygous |
| 13 | Silent | F556 | 1 | Heterozygous |
| 13 | Missense | R564L | 3 | Heterozygous |
| 13 | Missense | R564Q | 2 | Heterozygous |
| 13 | Missense | V567A | 1 | Heterozygous |
| 13 | Missense | G571S | 3 | Heterozygous |
| 13 | Missense | G571R | 1 | Heterozygous |
| 13 | Missense | L579F | 1 | Heterozygous |
| 13 | Missense | H587N | 1 | Heterozygous |
| 13 | Missense | S591L | 1 | Heterozygous |
| 14 | Deletion | S593-N622 | 2 | Heterozygous |
| 14 | Missense | H606Q | 1 | Heterozygous |
| 14 | Missense | V617F | >2000 | Hetero/Homo |
| 14 | Missense | V617I | 1 | Heterozygous |
| 14 | Missense | V617F C618R | 2 | Hetero/Homo |
| 14 | Missense | C618R | 1 | Heterozygous |
| 15 | Missense | L624P | 1 | Heterozygous |
| 15 | Missense | I645V | 1 | Heterozygous |

*Exon 12 (residues 511-547); Exon13 (residues 548-592); Exon14 (residues 593-622).

EXAMPLE 2

Additional JAK2 Mutations

Table 2 presents additional specific examples of novel JAK2 mutations identified by sequencing, along with their deduced amino acid substitutions.

TABLE 2

Exons 12, 13, 14, and 15 Mutations

| JAK2 Mutation Nucleic Acid; (Codon Change) | JAK2 Mutation Protein; (Amino Acid Change) |
|---|---|
| Exon 12 Missense Mutations ||
| c2035t; (acg > atg) | T514M; (Thr → Met) |
| a2091t; (aac > tac) | N533Y (Asn → Tyr) |

TABLE 2-continued

Exons 12, 13, 14, and 15 Mutations

| JAK2 Mutation Nucleic Acid; (Codon Change) | JAK2 Mutation Protein; (Amino Acid Change) |
|---|---|
| t2127c; (ttg > gtg) | L545V; (Leu → Val) |
| t2133c; (ttt > ctt) | F547L; (Phe → Leu) |
| del: deletion; ins: insertion | |
| Exon 13 Missense Mutations | |
| t2160g ttt > gtt | F556V (Phe → Val) |
| c2180t; (ggc > ggt) | G562 silent; (Gly) |
| g2185t; (cga > cta) | R564L; (Arg → Leu) |
| g2185a; (cga > caa) | R564Q; (Arg → Gln) |
| g2193t; (gta > tta) | V567L; (Val → Leu) |
| t2194c; (gta > gca) | V567A; (Val → Ala) |
| c2204t; (tac > tat) | Y570 Silent; (Tyr) |
| g2205a; (ggt > agt) | G571S; (Gly → Ser) |
| g2205c; (ggt > cgt) | G571R; (Gly → Arg) |
| c2229t; (ctt > ttt) | L579F; (Leu → Phe) |
| c2253a; (cac > aac) | H587N; (His → Asn) |
| c2266t; (tca > tta) | S591L; (Ser → Leu) |
| Exon 14 Missense and Deletion Mutations | |
| c2312a; (cac > caa) | H606Q; (His → Gln) |
| 2271-2358 (exon 14 deletion) | S593-N622 |
| Exon 15 Exon 15 Missense Mutations | |
| t2365c; (ctg > ccg) | L624P; (Leu → Pro) |
| a2427g; (ata > gta) | I645V; (Ile → Val) |

EXAMPLE 3

Characterization of the Exon 14 Deletion Mutation

Patients and Samples

In foregoing examples, over 10,000 samples from patients with suspected MPDs were tested for JAK2 mutations using direct sequencing of mRNA. A complete exon 14 deletion (nucleotides 2271-2358; amino acids S593-N622) was detected in <1% of cases with a JAK2 mutation. This mutation appears to be the result of an alternative splicing mutation, not detectable with DNA-based testing, that leads to a frameshift deletion in the JAK2 JH2 domain and expression of a truncated protein (S593I fsX8). In the initial study, this mutation was present at detectable levels (>15% of total JAK2 transcript) in a small proportion of MPD cases. Subsequently, the exon 14 deletion mutation was investigated for the possibility it may be expressed at low levels (<15% of JAK2 transcript) in patients with MPDs.

Peripheral blood samples from three groups of patients and healthy normal control subjects were tested. Group 1 comprised 61 consecutive randomly selected patients with confirmed non-CML MPD on the basis of clinical findings and complete peripheral blood and bone marrow analysis. The diagnosis of these patients was myelofibrosis in 27 (43%), polycythemia vera in 12 (19%), essential thrombocythemia in 6 (10%) and not-otherwise classified in 16 (27%). The other two patient groups were constructed from 183 residual de-identified samples from individuals with suspected non-CML MPDs initially submitted to Quest Diagnostics Nichols Institute for testing of JAK2 V617F as well as mutations in JAK2 exons 12 and 13: Group 2 comprised 90 samples that were negative for JAK2 mutations in V617 and exon 12 and 13, and Group 3 comprised 93 samples from patients with JAK2 V617F. Forty six normal healthy control individuals were also tested.

Plasma was separated from peripheral blood samples and used for extraction of total RNA. The mRNA was then used for detection of the JAK2 Δexon 14 variant by RT-PCR with bidirectional sequencing. All samples were also screened for the Δexon 14 transcript using a sensitive assay based on RT-PCR with fluorescent fragment analysis.

Sequence Analysis

Total nucleic acid was extracted from patient plasma or PB/BM cells using the NucliSens (BioMerieux, Durham, N.C.) extraction kit. The primer pair was designed to encompass JAK2 exons 12 through 14 and part of exon 15:

```
                                        (SEQ ID NO.: 12)
    5'-CTAAATGCTGTCCCCCAAAG-3' (forward);
    and (SEQ ID NO.: 13)
    5'-CCATGCCAACTGTTTAGCAA-3' (reverse).
```

The RT-PCR was performed using Superscript III one-step RT-PCR systems with Platinum Taq (Invitrogen, Carlsbad, Calif.) under the following thermocycler conditions: initial step of 94° C. for 2 minutes, followed by 40 cycles of 94° C. for 15 seconds, 60° C. for 30 seconds, and 68° C. for 1 minute, with a final extension step of 68° C. for 7 minutes. The 491-bp PCR product was then purified and sequenced in both forward and reverse directions using an ABI PRISM 3730XL Genetic Analyzer (Applied Biosystems, Foster City, Calif.). Sequencing data were base-called using sequencing analysis software and assembled and analyzed with SeqScape software (Applied Biosystems) using GenBank accession number NM 004972 (SEQ ID NO: 1) as reference.

Detection of JAK2 Δexon 14 Transcript Using Fragment Length Analysis

Total nucleic acid was extracted as described above from patient plasma or cells (peripheral blood or bone marrow). The primer pair was designed to encompass JAK2 exon 14, with the forward primer annealed in JAK2 exon 13 (5'-GAC TAC GGT CAA CTG CAT GAA A-3'; SEQ ID NO.: 14) and the reverse primer annealed in exon 16 (5'-CCA TGC CAA CTG TTT AGC AA-3'; SEQ ID NO.: 15). One of the two primers was FAM-labeled. The RT-PCR was performed using same buffer system (Invitrogen) and thermocycler conditions as the sequencing method. The JAK2 wild-type and Δexon 14 products were verified by determining the size of PCR products using the GeneScan 350ROX size standard (Applied Biosystems) and ABI PRISM 3730XL Genetic Analyzer. The wild-type product displays a 273-bp peak while the Δexon 14 splice variant displays a 185-bp peak (ie, 273-88 bp). The percentage of transcript accounted for by the JAK2 Δexon 14 splice mutant is calculated using the following formula:

Δexon 14/Total=Δexon 14 peak height (185 bp)/
    [Δexon 14 peak height (185 bp)+wildtype peak
    height (273 bp)]* 100

JAK2 Immunoprecipitation

Cells ($5 \times 10^5$-$1 \times 10^6$) were lysed in isotonic lysis buffer (150 mM NaCl, 20 mM Tris/HCl [pH 7.4], 0.3% Nonidet P-40, 12.5 mM β-glycerophosphate, 2 mM NaF, 200 mM $Na_3VO_4$, and 1 mM phenylmethylsulfonyl fluoride) containing 1× protease inhibitor mix (Roche Applied Science, Indianapolis, Ind.). Clarified lysates were subjected to immunoprecipitation using TrueBlot™ heads (Ebioscience, San Diego, Calif.) with an N-terminal anti-JAK2 antibody (JAK2-M126; Santa Cruz Biotechnology, Santa Cruz, Calif.). After incubation at 4° C. for 4 to 12 hours, immune complexes were washed 4 times in lysis buffer, separated by SDS/PAGE, and analyzed by immunoblotting using C-terminal JAK2 antibody (JAK2 [D2E12]; Cell Signaling Technology, Danvers, Mass.) or N-terminal JAK2 antibody (JAK2 N-17; Santa Cruz Biotechnology). K562 cell line (ATCC CCL-243 Manassas Va.) was used as negative control.

Immunoblot Analysis

Immunoblot analysis was performed as previously described (Bruey et al, Leuk Res. 2009). Briefly, equal amounts of immunoprecipitation products were separated by sodium dodecyl sulfate-polyacrylamide gel electrophoresis (SDS-PAGE), and the gels were electrophoretically trans- 51 of the 183 patients with suspected MPDs (27%) overall, including 20 of the 93 (22%) V617-positive patients (mean [range] expression=5.41% [2.13%-26.22%]) and 31 of the 90 (34%) V617F-negative patients (mean expression=3.88% [2.08%-12.22%]. There is a strong tendency (p=0.07) of finding Δexon 14 in unmutated patients. None of the 46 plasma RNA samples from the normal control group showed any expression of the Δexon 14 transcript. Most patients with Δexon 14-positive in each group had expression levels below 15%, therefore, it is frequently missed by direct sequencing.

TABLE 3

Prevalence and Relative Level of the Δexon 14 JAK2 Transcript in Patients with Suspected or Confirmed Myeloproliferative Neoplasms (MPDs)

| | Suspected MPD (n = 183) | | | | Confirmed MPD (n = 61) | |
|---|---|---|---|---|---|---|
| | V617F-Negative (n = 90) | | V617F-Positive (n = 93) | | | |
| | n (%) | Mean (range) percentage of JAK2 transcript | n (%) | Mean (range) percentage of JAK2 transcript | n (%) | Mean (range) percentage of JAK2 transcript |
| Δexon 14 | 31 (34) | 3.88 (2.08-12.22) | 20 (22) | 5.41 (2.13-26.22) | 9 (15) | 12.04 (3.96-33.85) |
| No Δexon 14 | 59 (66) | NA | 73 (78) | NA | 52 (85) | NA | ferred to nitrocellulose membranes (0.2-mm pore size; Whatman, Florham Park, N.J.). The blots were blocked with 5% bovine serum albumin in Tris-buffered saline with 0.05% Tween-20 (TBS-Tween) for 2 hours. The membrane was incubated with primary antibody for 5 hours at 4° C., washed with TBS-Tween, and incubated with secondary antibody for 30 minutes at room temperature (TrueBlot™, Ebioscience). After additional washing in TBS-Tween, chemiluminescent reagent (ECL; GE Healthcare, Piscataway, N.J.) was added and the image was developed on x-ray film.

Detection and Prevalence of JAK2 Δexon 14 Transcript

Figure 3:
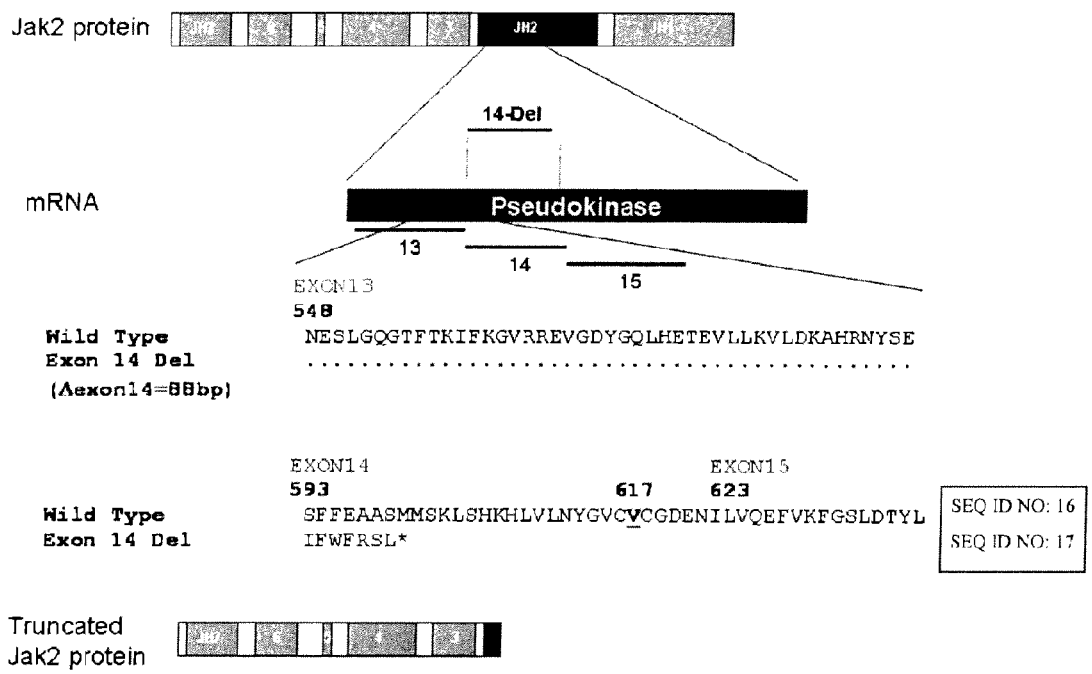
FIG. 3 is a schematic showing the JAK2 Δexon 14 mutation. Top, schematic diagram of the JAK2 protein showing JAK homology domains 1 through 7 (JH1-JH7) with the JH2 pseudokinase domain highlighted in black. The corresponding exon regions of the mRNA is shown with the exons 13, 14, and 15. Because exon 14 is consists of 88 bp, its deletion leads to frameshift and early termination of translation after coding for seven new amino acids and elimination of the V617 codon of JAK2 (lower panel). The wildtype (SEQ ID NO: 16) and resulting truncated (SEQ ID NO: 17) JAK2 protein is shown on the bottom.
Figure 4:
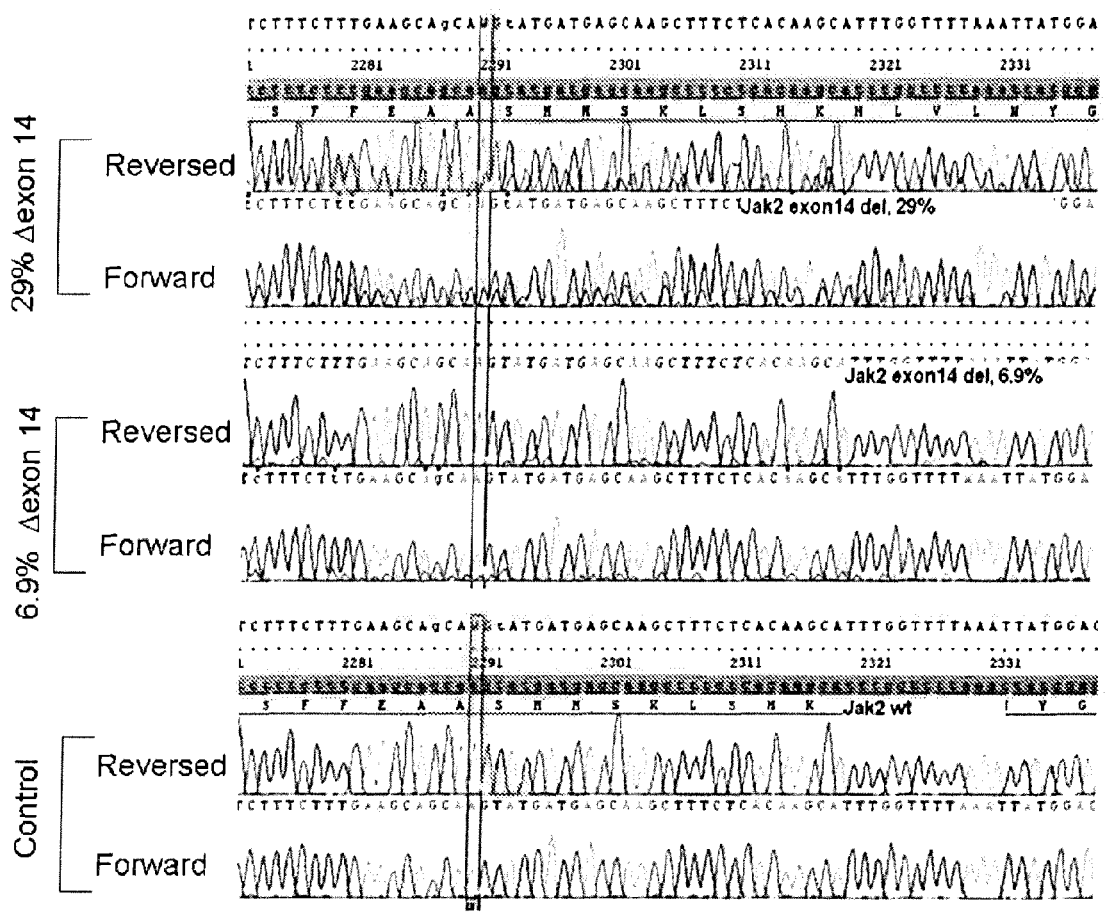
FIG. 4 is a series of sequencing chromatograms of the Δexon 14 JAK2 mutation generated using bi-directional sequencing in samples having high levels (29%) and low levels (6.9%) of Δexon 14 transcript.
Figure 5:
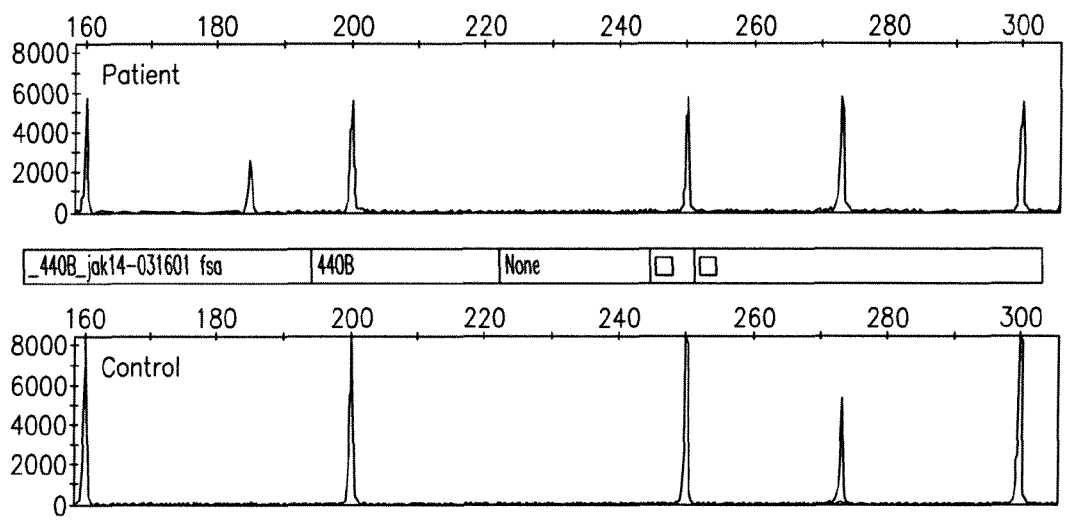
FIG. 5 shows the result of assessing JAK2 exon 14 by RT-PCR with fragment length analysis, as described in Example 3. The expected 273-bp (full-length) amplification product is observed in both the patient and control samples, but the patient sample confirms an additional peak at 185-bp which corresponds to the truncated Δexon 14 transcript. The remaining peaks that are common to both samples are the exogenously-added size markers.
Figure 6:
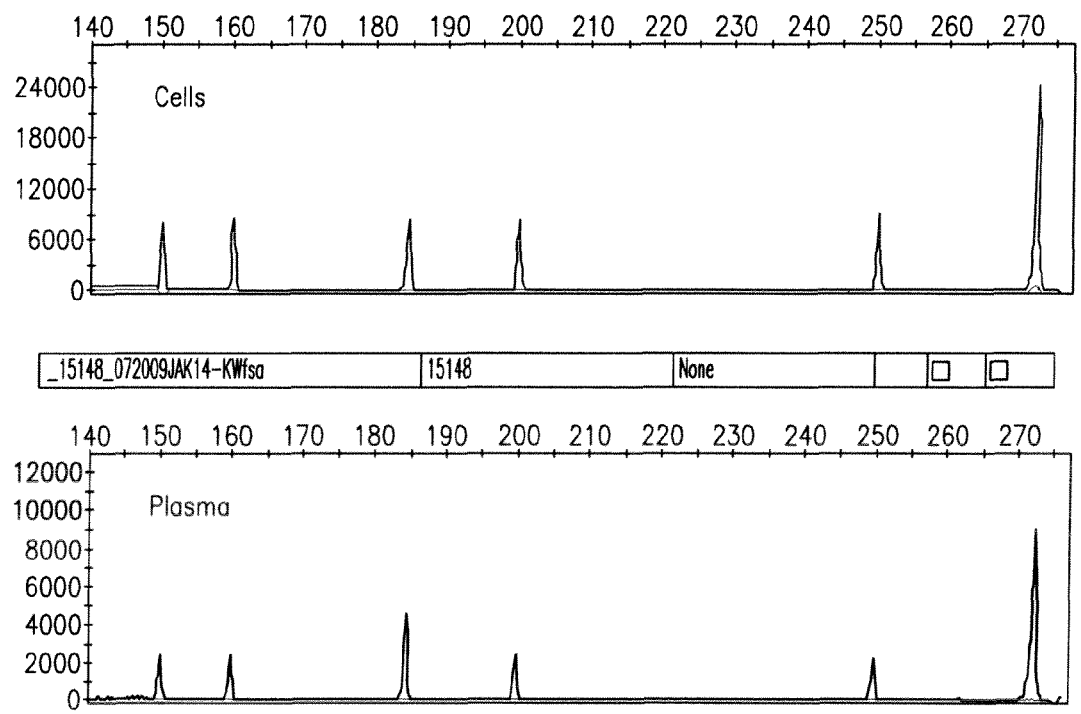
FIG. 6 shows the result of assessing JAK2 exon 14 by RT-PCR with fragment length analysis on RNA obtained from plasma or peripheral blood cells of patients, as described in Example 3.

When JAK2 RNA (not DNA) is used for direct sequencing, the Δexon 14 transcript is reliably detected if present at levels >15% to 20% of total JAK2 RNA (FIGS. 3 and 4). MPN patients rarely have Δexon 14 transcript levels above this threshold, and the results of direct sequence analysis can be difficult to interpret in patients with apparent low-level expression. In these cases, the Δexon 14 transcript can easily be interpreted as background or poor sequencing if the background sequence is not read completely and aligned to the JAK2 sequence (FIG. 4). To more accurately detect low levels of Δexon 14 transcript expression, an RT-PCR based assay with fluorescent fragment length analysis was developed. With this method, the JAK2 Δexon 14 splice variant shows a 185-bp fragment while the wild-type shows a 273-bp fragment (FIG. 5). To confirm that the Δexon 14 splice variant that is detected in plasma is actually present in cells, we analyzed paired cell and plasma RNA from patients previously confirmed to show expression of the Δexon 14 transcript in plasma. Both plasma and cells revealed reliable results for detecting Δexon 14 transcripts (FIG. 6).

Figure 7:
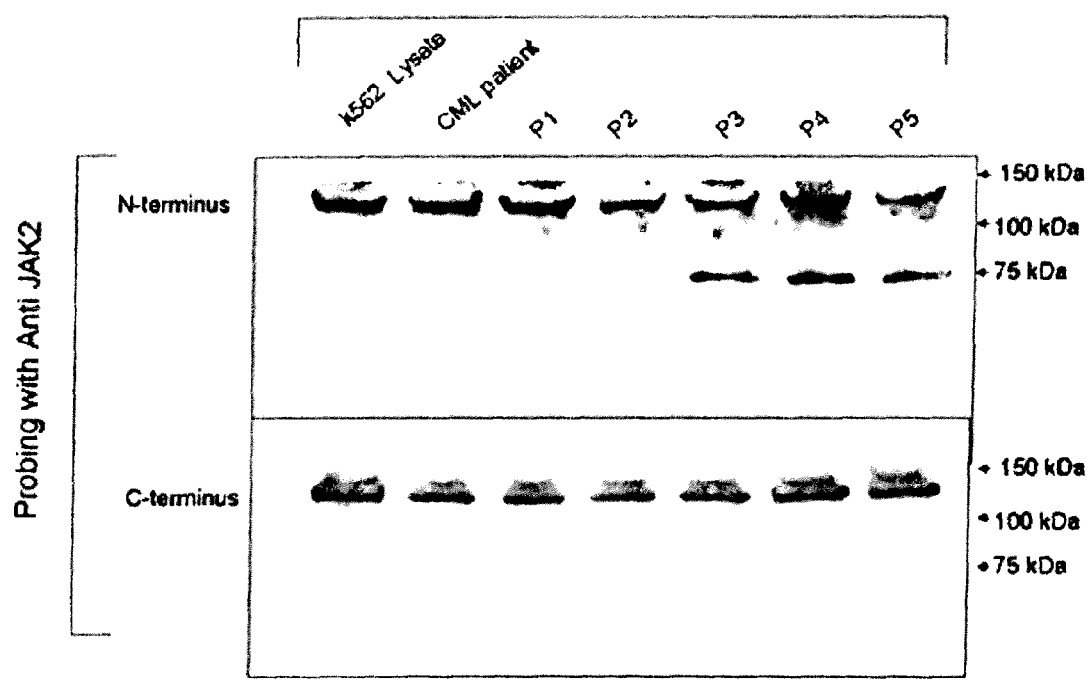
FIG. 7 is a photomicrograph of an electrophoretic gel showing the truncated JAK2 protein resulting from JAK2 Δexon 14 mutation in patients with chronic myeloproliferative neoplasms. Lysates were prepared from the indicated human CML K562 cell line (Lane 1), a patient with chronic myelogenous leukemia (lane 2), and 5 patients with chronic MPDs (Lanes 3-7). Patient 1: non-CML CMPD, JAK2 V617F positive; Patient 2: non-CML CMPD, JAK2 V617F negative; Patient 3: non-CML CMPD, JAK2 Δexon 14-positive; Patient 4: non-CML CMPD, JAK2 Δexon 14-positive; Patient 5: non-CML CMPD, JAK2 Δexon 14-positive. Top Panel: Probing with an anti-JAK2 N-terminal clone yielded a wild-type JAK2 band at 130 kDa in the K562 and other negative control lanes, and an additional band at 75 kDa only in patients with expression of Δexon 14 transcript. Bottom Panel: An anti-JAK2 clone directed against the carboxyl-terminus of JAK2 yielded only a single band at 130 kDa.

Using the RT-PCR/fragment length analysis assay, we screened all groups of patients. Samples with Δexon 14 mutant to wild-type ratios greater than 15% by fragment analysis were tested and successfully confirmed by careful inspection of direct sequencing results. The Δexon 14 was detected in 9 of the 61 confirmed MPD patients (15%) (Table 3), where it accounted for 3.96% to 33.85% (mean=12.04%) of JAK2 transcript. In this group of patients, Δexon 14 was detected in 33.3% of V617F-positive patients and in 57.9% of V617F-negative patients. This mutation was also detected in Effects of Δexon 14 on JAK2 Protein As indicated in FIG. 3, deletion of exon 14 leads to a complete deletion of codon V617, a hot spot for mutation in patients with non-CML MPDs. More importantly, since exon 14 is composed of 88 bp, its deletion leads to a frameshift and the coding of new amino acids. However, the frame shift results in the addition of only 7 new amino acids, followed by a termination codon leading to truncation of the JAK2 protein within the pseudokinase domain. Therefore, we used immunoprceipitation and immunoblotting to confirm that the truncated JAK2 protein is expressed in cells from patients with confirmed JAK2 Δexon 14 transcripts (FIG. 7). Total JAK2 protein was immunoprecipitated using anti-JAK2 (N-terminal) antibody. For negative controls we used the K562 CML cell line, which does not express JAK2 Δexon 14, in addition to cell samples from 1) a patient with CML; and 2) two patients with MPD who had been confirmed by RT/PCR to be negative for Δexon 14 transcripts. Cells from three patients with different levels of Δexon 14 transcript expression, as confirmed by RT/PCR, were used as positive samples.

Probing with the anti-JAK2 N-terminal clone yielded a wildtype JAK2 band at 130 kDa in the K562 and other negative control lanes, and an additional band at 75 kDa only in patients with confirmed expression of the Δexon 14 transcript (FIG. 7). This additional immunoprecipitation product represents the truncated JAK2 protein. The use of another anti-JAK2 clone directed against the carboxyl-terminus of JAK2, which is deleted from the truncated JAK2 protein, yielded a single band at 130 kDa, showing specificity of detection of the truncated JAK2 Dexon 14 protein (FIG. 7). Lysates from the K562 cell line and the CML patient showed only the wild-type band at 130 kDa. This confirms that the Δexon 14 transcripts are translated.

These findings confirm that many individuals with non-CML MPDs, especially those lacking V617F, express low levels of the JAK2 Δexon 14. The paucity of reports of the Δexon 14 variant in MPD patients most likely derives from the fact that JAK2 mutation assays typically rely on DNA rather than RNA. Furthermore, this abnormality cannot be detected with methods that rely on use of specific probes.

Bi-directional sequencing of mRNA transcript can detect most mutations, including splice variants. However, this approach may not provide the same sensitivity as the fluorescent fragment analysis method described herein for detecting low levels of this variant. The fact that the JAK2 Δexon 14 transcript is a fraction of the total JAK2 transcript is, most likely, due to either alternative splicing or a mutation in the DNA in small fraction of the clone.

The fact that the JAK2 Δexon 14 is detected only in patients with MPDs, and more likely in patients negative for V617F (57.9% vs. 33.3%) (P=0.07), demonstrates that it plays a significant role in the pathophysiology of MPDs. All currently identified JAK2 mutations, including point mutations and insertions/deletions ("indels") in exons 12 through 15, reside in the pseudokinase domain (JH2)-coding region of JAK2 and do not affect the reading frame. The JH2 domain is usually in close proximity to the kinase domain (JH1), inhibiting its activation if not bound to an active receptor. Mutations in the JH2 domain may thus lead to constitutive activation of the JAK2 protein; it is believed that mutations in the JH2 domain cause constitutive activation in the downstream JAK2-STAT signaling pathways as long as the JAK2 is bound to the receptor. Deletion within the JH2 domain and complete deletion of the kinase domain (JH1) is unexpected and raises questions on its mechanism in activating the JAK2-STAT pathway. The Δexon 14 mutation preserves the JAK2 FERM domain (JH4-7), which is responsible for association with growth factor (eg, erythropoietin and thrombopoietin) receptors. It is thus possible that the truncated JAK2 dimerizes with wild-type JAK2 to influence its structure, activating its kinase domain and the JAK2-STAT pathway. It is also possible that the Δexon 14 mutation causes activation of STAT5 by altering receptor binding of the FERM domain.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for diagnosing a human individual as having a myeloproliferative disease, the method comprising:
   a) providing a biological sample from the individual, wherein the sample comprises JAK2 mRNA;
   b) evaluating the JAK2 mRNA from the sample to detect the absence of exon 14; and
   c) diagnosing the individual as having a myeloproliferative disease if the nucleotide sequence exon 14 is identified as being absent.

2. The method of claim 1, wherein the sample is evaluated to determine the deletion of the nucleotide sequence corresponding to nucleotides 2271-2358 of SEQ ID NO: 1 in the JAK2 mRNA.

3. The method of claim 1, wherein oligonucleotide primers which flank exon 14 are used to detect the absence of exon 14.

4. The method of claim 3, wherein the JAK2 mRNA is evaluated to determine whether the nucleotide sequence encoding exon 14 is absent by evaluating the length of an amplification product.

5. The method of claim 4, wherein the JAK2 mRNA is identified as having an exon 14 deletion when the amplification product is at least 88 nucleotides shorter than the amplification product produced from a JAK2 mRNA containing an intact exon 14 coding sequence.

6. The method of claim 1, wherein the relative proportion of JAK2 mRNA containing the exon 14 deletion is determined.

7. The method of claim 1, wherein said sample is selected from the group consisting of blood, serum, and plasma.

8. The method of claim 1, wherein said JAK2 mRNA further comprises at least one additional mutation shown in Table 2.

9. The method of claim 1, wherein JAK2 mRNA in said biological sample is sequenced.

* * * * *